United States Patent
Hasegawa et al.

(10) Patent No.: US 9,519,341 B2
(45) Date of Patent: Dec. 13, 2016

(54) MEDICAL MANIPULATOR AND SURGICAL SUPPORT APPARATUS

(75) Inventors: Mitsuaki Hasegawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1138 days.

(21) Appl. No.: 13/566,047

(22) Filed: Aug. 3, 2012

(65) Prior Publication Data

US 2013/0041219 A1 Feb. 14, 2013

Related U.S. Application Data

(60) Provisional application No. 61/515,203, filed on Aug. 4, 2011.

(51) Int. Cl.
*A61B 17/00* (2006.01)
*A61B 19/00* (2006.01)
(Continued)

(52) U.S. Cl.
CPC .............. *G06F 3/01* (2013.01); *A61B 17/29* (2013.01); *A61B 17/32002* (2013.01);
(Continued)

(58) Field of Classification Search
USPC ....... 600/101, 102, 104, 106, 117, 118, 417, 600/429; 606/1, 130, 205; 74/490.01–490.06; 700/245–264
See application file for complete search history.

(56) References Cited

U.S. PATENT DOCUMENTS

| | | |
|---|---|---|
| 3,139,990 A | 7/1964 | Jelatis et al. |
| 3,923,166 A | 12/1975 | Fletcher et al. |

(Continued)

FOREIGN PATENT DOCUMENTS

| | | |
|---|---|---|
| CN | 101027010 A | 8/2007 |
| CN | 101167658 A | 4/2008 |

(Continued)

OTHER PUBLICATIONS

Office Action dated Nov. 19, 2015 received in related U.S. Appl. No. 14/157,920.

(Continued)

*Primary Examiner* — Ryan Henderson
(74) *Attorney, Agent, or Firm* — Scully, Scott, Murphy & Presser, P.C.

(57) ABSTRACT

A medical manipulator includes: a holding portion whose proximal end portion is fixed to a base; a positioning portion that has a fixing portion that is fixed to a distal end portion of the holding portion, and that is formed such that a treatment portion of a surgical instrument is able to move relative to the fixing portion; a reference orientation detecting portion that detects an orientation of a reference position on the positioning portion; a drive section that is used to move the treatment portion relative to the fixing portion; and a displacement detecting section that detects an amount of movement, including angular displacement, of the treatment portion relative to the reference position, and that calculates as the orientation on the treatment portion an orientation that is different by an amount of angular displacement that it has itself detected from the orientation on the reference position detected by the reference orientation detecting portion.

6 Claims, 14 Drawing Sheets

(51) Int. Cl.
  *A61B 1/00*      (2006.01)
  *A61B 1/04*      (2006.01)
  *B25J 9/18*      (2006.01)
  *G05B 19/19*     (2006.01)
  *B25J 15/02*     (2006.01)
  *G05B 19/04*     (2006.01)
  *B25J 17/00*     (2006.01)
  *B25J 17/02*     (2006.01)
  *B25J 18/00*     (2006.01)
  *G06F 3/01*      (2006.01)
  *A61B 17/29*     (2006.01)
  *A61B 17/32*     (2006.01)
  *A61B 18/14*     (2006.01)
  *B25J 13/02*     (2006.01)
  *A61B 17/068*    (2006.01)

(52) U.S. Cl.
  CPC .......... *A61B 18/1402* (2013.01); *A61B 34/30* (2016.02); *A61B 34/37* (2016.02); *A61B 34/74* (2016.02); *A61B 34/76* (2016.02); *A61B 34/77* (2016.02); *A61B 46/10* (2016.02); *A61B 90/50* (2016.02); *B25J 13/02* (2013.01); *A61B 17/068* (2013.01); *A61B 34/20* (2016.02); *A61B 34/25* (2016.02); *A61B 46/23* (2016.02); *A61B 2017/00119* (2013.01); *A61B 2017/00477* (2013.01); *A61B 2017/00482* (2013.01); *A61B 2034/2055* (2016.02); *A61B 2034/2065* (2016.02); *A61B 2090/065* (2016.02); *A61B 2090/067* (2016.02); *A61B 2090/0803* (2016.02); *A61B 2090/0813* (2016.02); *A61B 2090/0814* (2016.02); *A61B 2090/364* (2016.02); *A61B 2090/3937* (2016.02); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | | |
|---|---|---|---|
| 4,672,281 A | 6/1987 | Yagusic et al. |
| 4,830,569 A | 5/1989 | Jannborg |
| 4,872,803 A | 10/1989 | Asakawa |
| 5,214,969 A | 6/1993 | Adkins et al. |
| 5,603,723 A | 2/1997 | Aranyi et al. |
| 5,632,432 A | 5/1997 | Schulze et al. |
| 5,649,956 A | 7/1997 | Jensen et al. |
| 5,656,903 A | 8/1997 | Shui et al. |
| 5,712,543 A | 1/1998 | Sjostrom |
| 5,760,530 A | 6/1998 | Kolesar |
| 5,762,458 A | 6/1998 | Wang et al. |
| 5,784,542 A | 7/1998 | Ohm et al. |
| 5,817,119 A | 10/1998 | Klieman et al. |
| 5,836,869 A | 11/1998 | Kudo et al. |
| 5,855,583 A | 1/1999 | Wang et al. |
| 5,871,493 A | 2/1999 | Sjostrom et al. |
| 5,876,325 A | 3/1999 | Mizuno et al. |
| 6,007,550 A | 12/1999 | Wang et al. |
| 6,063,095 A | 5/2000 | Wang et al. |
| 6,082,797 A | 7/2000 | Antonette |
| 6,090,122 A | 7/2000 | Sjostrom et al. |
| 6,102,850 A | 8/2000 | Wang et al. |
| 6,132,368 A | 10/2000 | Cooper |
| 6,132,441 A | 10/2000 | Grace |
| 6,206,903 B1 | 3/2001 | Ramans |
| 6,246,200 B1 | 6/2001 | Blumenkranz et al. |
| 6,328,752 B1 | 12/2001 | Sjostrom et al. |
| 6,346,072 B1 | 2/2002 | Cooper |
| 6,430,473 B1 | 8/2002 | Lee et al. |
| 6,436,107 B1 | 8/2002 | Wang et al. |
| 6,441,577 B2 | 8/2002 | Blumenkranz et al. |
| 6,557,558 B1 | 5/2003 | Tajima et al. |
| 6,574,355 B2 | 6/2003 | Green |
| 6,587,750 B2 | 7/2003 | Gerbi et al. |
| 6,602,185 B1 | 8/2003 | Uchikubo |
| 6,645,196 B1 | 11/2003 | Nixon et al. |
| 6,666,876 B2 | 12/2003 | Kawai et al. |
| 6,676,684 B1 | 1/2004 | Morley et al. |
| 6,685,698 B2 | 2/2004 | Morley et al. |
| 6,699,177 B1 | 3/2004 | Wang et al. |
| 6,746,443 B1 | 6/2004 | Morley et al. |
| 6,783,524 B2 | 8/2004 | Anderson et al. |
| 6,786,896 B1 | 9/2004 | Madhani et al. |
| 6,853,879 B2 | 2/2005 | Sunaoshi |
| 6,866,671 B2 | 3/2005 | Tierney et al. |
| 6,905,460 B2 | 6/2005 | Wang et al. |
| 6,913,613 B2 | 7/2005 | Schwarz et al. |
| 7,083,571 B2 | 8/2006 | Wang et al. |
| 7,101,363 B2 | 9/2006 | Nishizawa et al. |
| 7,107,124 B2 | 9/2006 | Green |
| 7,118,582 B1 | 10/2006 | Wang et al. |
| 7,273,488 B2 | 9/2007 | Nakamura et al. |
| 7,295,893 B2 | 11/2007 | Sunaoshi |
| 7,313,464 B1 | 12/2007 | Perreault et al. |
| 7,331,967 B2 | 2/2008 | Lee et al. |
| 7,357,774 B2 | 4/2008 | Cooper |
| 7,373,219 B2 | 5/2008 | Nowlin et al. |
| 7,422,592 B2 | 9/2008 | Morley et al. |
| 7,476,237 B2 | 1/2009 | Taniguchi et al. |
| 7,549,998 B2 | 6/2009 | Braun |
| 7,594,912 B2 | 9/2009 | Cooper et al. |
| 7,608,083 B2 | 10/2009 | Lee et al. |
| 7,654,431 B2 | 2/2010 | Hueil et al. |
| 7,666,191 B2 | 2/2010 | Orban, III et al. |
| 7,674,255 B2 | 3/2010 | Braun |
| 7,695,481 B2 | 4/2010 | Wang et al. |
| 7,699,835 B2 | 4/2010 | Lee et al. |
| 7,699,855 B2 | 4/2010 | Anderson et al. |
| 7,778,733 B2 | 8/2010 | Nowlin et al. |
| 7,819,884 B2 | 10/2010 | Lee et al. |
| 7,819,885 B2 | 10/2010 | Cooper |
| 7,862,579 B2 | 1/2011 | Ortiz et al. |
| 7,865,266 B2 | 1/2011 | Moll et al. |
| 7,955,321 B2 | 6/2011 | Kishi et al. |
| 8,105,320 B2 | 1/2012 | Manzo |
| 8,155,479 B2 | 4/2012 | Hoffman et al. |
| 8,267,958 B2 | 9/2012 | Braun |
| 8,350,806 B2 | 1/2013 | Nagasaka et al. |
| 8,423,186 B2 | 4/2013 | Itkowitz et al. |
| 8,460,277 B2 | 6/2013 | Suarez et al. |
| 8,496,647 B2 | 7/2013 | Blumenkranz et al. |
| 8,540,748 B2 | 9/2013 | Murphy et al. |
| 8,744,137 B2 | 6/2014 | Sakai et al. |
| 8,845,681 B2 | 9/2014 | Grace |
| 8,876,858 B2 | 11/2014 | Braun |
| 8,888,789 B2 | 11/2014 | Prisco et al. |
| 8,903,549 B2 | 12/2014 | Itkowitz et al. |
| 8,906,002 B2 | 12/2014 | Kishi et al. |
| 9,039,681 B2 | 5/2015 | Wang et al. |
| 9,283,675 B2 | 3/2016 | Hager et al. |
| 9,308,009 B2 | 4/2016 | Madan et al. |
| 9,308,646 B2 | 4/2016 | Lim et al. |
| 2001/0021859 A1 | 9/2001 | Kawai et al. |
| 2001/0055062 A1 | 12/2001 | Shioda et al. |
| 2002/0072736 A1 | 6/2002 | Tierney et al. |
| 2002/0091374 A1 | 7/2002 | Cooper |
| 2002/0128552 A1 | 9/2002 | Nowlin et al. |
| 2003/0033024 A1 | 2/2003 | Sunaoshi |
| 2003/0060927 A1 | 3/2003 | Gerbi et al. |
| 2003/0069471 A1 | 4/2003 | Nakanishi et al. |
| 2003/0083648 A1 | 5/2003 | Wang et al. |
| 2003/0100817 A1 | 5/2003 | Wang et al. |
| 2003/0216723 A1 | 11/2003 | Shinmura et al. |
| 2004/0049205 A1 | 3/2004 | Lee et al. |
| 2004/0092912 A1 | 5/2004 | Jinno et al. |
| 2004/0111113 A1 | 6/2004 | Nakamura et al. |
| 2004/0140787 A1 | 7/2004 | Okamoto et al. |
| 2004/0186345 A1 | 9/2004 | Yang et al. |
| 2004/0186624 A1 | 9/2004 | Oda et al. |

(56) References Cited

U.S. PATENT DOCUMENTS

| | | |
|---|---|---|
| 2004/0243147 A1 | 12/2004 | Lipow |
| 2004/0246469 A1* | 12/2004 | Hirose .............. A61B 1/00048 356/139.03 |
| 2005/0020876 A1 | 1/2005 | Shioda et al. |
| 2005/0021050 A1 | 1/2005 | Cooper |
| 2005/0033117 A1 | 2/2005 | Ozaki et al. |
| 2005/0125027 A1 | 6/2005 | Knodel et al. |
| 2005/0149003 A1 | 7/2005 | Tierney et al. |
| 2005/0228365 A1 | 10/2005 | Wang et al. |
| 2005/0273086 A1 | 12/2005 | Green et al. |
| 2006/0052664 A1 | 3/2006 | Julian et al. |
| 2006/0074408 A1 | 4/2006 | Jinno et al. |
| 2006/0079865 A1 | 4/2006 | Jinno et al. |
| 2006/0079866 A1 | 4/2006 | Jinno et al. |
| 2006/0087746 A1 | 4/2006 | Lipow |
| 2006/0116973 A1 | 6/2006 | Okamoto et al. |
| 2006/0149162 A1 | 7/2006 | Daw et al. |
| 2006/0155262 A1 | 7/2006 | Kishi et al. |
| 2006/0161138 A1 | 7/2006 | Orban, III et al. |
| 2006/0190031 A1 | 8/2006 | Wales et al. |
| 2006/0235436 A1 | 10/2006 | Anderson et al. |
| 2007/0012135 A1 | 1/2007 | Tierney et al. |
| 2007/0089557 A1 | 4/2007 | Solomon et al. |
| 2007/0119274 A1 | 5/2007 | Devengenzo et al. |
| 2007/0137372 A1 | 6/2007 | Devengenzo et al. |
| 2007/0138992 A1 | 6/2007 | Prisco et al. |
| 2007/0142823 A1 | 6/2007 | Prisco et al. |
| 2007/0142825 A1 | 6/2007 | Prisco et al. |
| 2007/0156122 A1 | 7/2007 | Cooper |
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1 | 9/2007 | Takahashi et al. |
| 2007/0225550 A1 | 9/2007 | Gattani et al. |
| 2007/0249897 A1 | 10/2007 | Miyamoto et al. |
| 2007/0265638 A1 | 11/2007 | Lipow et al. |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0132088 A1 | 5/2009 | Taitler |
| 2009/0163948 A1 | 6/2009 | Sunaoshi et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0281378 A1 | 11/2009 | Banju et al. |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1 | 6/2010 | Yoshie |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0225209 A1 | 9/2010 | Goldberg et al. |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | van den Dool et al. |
| 2011/0190932 A1 | 8/2011 | Tsusaka et al. |
| 2011/0230894 A1 | 9/2011 | Simaan et al. |
| 2011/0238079 A1 | 9/2011 | Hannaford et al. |
| 2011/0276058 A1 | 11/2011 | Choi et al. |
| 2011/0279374 A1 | 11/2011 | Park et al. |
| 2011/0282493 A1 | 11/2011 | Ortmaier |
| 2011/0288579 A1 | 11/2011 | Hyodo |
| 2011/0306952 A1 | 12/2011 | Chen et al. |
| 2012/0071752 A1 | 3/2012 | Sewell et al. |
| 2012/0165828 A1 | 6/2012 | Duque et al. |
| 2012/0191245 A1 | 7/2012 | Fudaba et al. |

FOREIGN PATENT DOCUMENTS

| | | |
|---|---|---|
| CN | 101426412 A | 5/2009 |
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2 332 484 A2 | 6/2011 |
| JP | 63-29810 A | 2/1988 |
| JP | 64-34688 A | 2/1989 |
| JP | 1-271185 A | 10/1989 |
| JP | 2-71980 A | 3/1990 |
| JP | 2-292193 A | 12/1990 |
| JP | 3-161289 A | 7/1991 |
| JP | 5-96477 A | 4/1993 |
| JP | 5-329784 A | 12/1993 |
| JP | 7-1366 A | 1/1995 |
| JP | 7-194609 A | 8/1995 |
| JP | 7-241300 A | 9/1995 |
| JP | 7-246578 A | 9/1995 |
| JP | 7-96182 B2 | 10/1995 |
| JP | 8-66883 A | 3/1996 |
| JP | 8-215204 A | 8/1996 |
| JP | 8-243080 A | 9/1996 |
| JP | H10-502265 A | 3/1998 |
| JP | 10-128538 A | 5/1998 |
| JP | 11-300662 A | 11/1999 |
| JP | 2000-312684 A | 11/2000 |
| JP | 2001-087281 | 4/2001 |
| JP | 2001-113481 A | 4/2001 |
| JP | 2001-277157 | 10/2001 |
| JP | 2001-277157 A | 10/2001 |
| JP | 2001-309920 A | 11/2001 |
| JP | 2002-014287 | 1/2002 |
| JP | 2002-59380 A | 2/2002 |
| JP | 2002-102248 A | 4/2002 |
| JP | 2002-272758 A | 9/2002 |
| JP | 2002-537884 A | 11/2002 |
| JP | 2003-24336 A | 1/2003 |
| JP | 2003-53685 A | 2/2003 |
| JP | 2003-250812 A | 9/2003 |
| JP | 2003-265500 A | 9/2003 |

(56) References Cited

FOREIGN PATENT DOCUMENTS

| | | |
|---|---|---|
| JP | 2003-340752 A | 12/2003 |
| JP | 2004-105451 A | 4/2004 |
| JP | 2004-114201 A | 4/2004 |
| JP | 2005-511185 A | 4/2005 |
| JP | 3686947 | 6/2005 |
| JP | 2005-192743 A | 7/2005 |
| JP | 2005-261827 | 9/2005 |
| JP | 2005-283600 A | 10/2005 |
| JP | 2005-312991 A | 11/2005 |
| JP | 2006-61272 A | 3/2006 |
| JP | 2006-167867 A | 6/2006 |
| JP | 2006-288955 A | 10/2006 |
| JP | 2006-321027 A | 11/2006 |
| JP | 2007-29274 A | 2/2007 |
| JP | 2007-38315 A | 2/2007 |
| JP | 2007-98507 A | 4/2007 |
| JP | 2007-105485 A | 4/2007 |
| JP | 3999816 B2 | 10/2007 |
| JP | 4058113 | 12/2007 |
| JP | 2008-282 A | 1/2008 |
| JP | 2008-36793 A | 2/2008 |
| JP | 2008-093270 A | 4/2008 |
| JP | 2008-104854 A | 5/2008 |
| JP | 2008-514357 A | 5/2008 |
| JP | 2008-173724 A | 7/2008 |
| JP | 4129313 B2 | 8/2008 |
| JP | 4176126 | 8/2008 |
| JP | 2009-028157 A | 2/2009 |
| JP | 2009-56164 A | 3/2009 |
| JP | 2009-512514 | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226029 A | 10/2009 |
| JP | 2009-226093 | 10/2009 |
| JP | 2009-269127 A | 11/2009 |
| JP | 2010-504127 A | 2/2010 |
| JP | 2010-076012 | 4/2010 |
| JP | 2010-524548 A | 7/2010 |
| JP | 2011-509112 A | 3/2011 |
| JP | 2011-206213 A | 10/2011 |
| JP | 2012-000199 A | 1/2012 |
| JP | 2012-12104 A | 1/2012 |
| JP | 2012-091310 | 5/2012 |
| JP | 2012-91310 A | 5/2012 |
| WO | 96/00044 A1 | 1/1996 |
| WO | 97/16123 A1 | 5/1997 |
| WO | 97/16124 A1 | 5/1997 |
| WO | 97/29690 A1 | 8/1997 |
| WO | 98/25666 A1 | 6/1998 |
| WO | 00/51486 A1 | 9/2000 |
| WO | 00/60421 A2 | 10/2000 |
| WO | 03/049596 A2 | 6/2003 |
| WO | 2006/039092 A2 | 4/2006 |
| WO | 2006/111966 A2 | 10/2006 |
| WO | 2007/047782 A2 | 4/2007 |
| WO | WO 2007/047782 A2 | 4/2007 |
| WO | 2007/075864 A1 | 7/2007 |
| WO | WO 2007/111955 A2 | 10/2007 |
| WO | WO 2007/126443 A2 | 11/2007 |
| WO | 2007/138674 A1 | 12/2007 |
| WO | 2008/038184 A2 | 4/2008 |
| WO | 2008/108289 A1 | 9/2008 |
| WO | 2009/034477 A2 | 3/2009 |
| WO | 2009/089614 A1 | 7/2009 |
| WO | 2010/006057 A1 | 1/2010 |
| WO | 2010/093152 A2 | 8/2010 |
| WO | 2010/109932 A1 | 9/2010 |
| WO | 2010/126127 A1 | 11/2010 |
| WO | 2011/025786 A1 | 3/2011 |
| WO | 2011/060139 A2 | 5/2011 |
| WO | 2011/060185 A1 | 5/2011 |
| WO | 2011/060187 A1 | 5/2011 |
| WO | 2011/085815 A1 | 7/2011 |
| WO | WO 2012/042949 A1 | 4/2012 |

OTHER PUBLICATIONS

International Search Report dated Oct. 23, 2012 from related International Application No. PCT/JP2012/070414.
International Search Report dated Sep. 4, 2012 from related International Application No. PCT/JP2012/070408.
International Search Report dated Aug. 28, 2012 from related International Application No. PCT/JP2012/069927.
International Search Report dated Sep. 4, 2012 from related International Application No. PCT/JP2012/070415.
International Search Report dated Oct. 16, 2012 from related International Application No. PCT/JP2012/070581.
International Search Report dated Nov. 13, 2012 from related International Application No. PCT/JP2012/070576.
International Search Report dated Sep. 18, 2012 from related International Application No. PCT/JP2012/070417.
International Search Report dated Oct. 30, 2012 from related International Application No. PCT/JP2012/070418.
International Search Report dated Sep. 11, 2012 from related International Application No. PCT/JP2012/070416.
International Search Report dated Sep. 18, 2012 from related International Application No. PCT/JP2012/070407.
International Search Report dated Sep. 18, 2012 from related International Application No. PCT/JP2012/069868.
International Search Report dated Nov. 6, 2012 from related International Application No. PCT/JP2012/069919.
International Search Report dated Sep. 11, 2012 from related International Application No. PCT/JP2012/069696.
U.S. Office Action dated Apr. 9, 2015 received in related U.S. Appl. No. 14/169,675.
U.S. Office Action dated May 8, 2015 received in related U.S. Appl. No. 14/157,920.
Chinese Office Action dated Jun. 3, 2015 from related Chinese Application No. 201280035926.3, together with an English language translation.
Chinese Office Action dated Jul. 1, 2015 from related Chinese Application No. 201280037244.6, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Extended Supplementary European Search Report dated Jul. 23, 2015 from related European Application No. 12 81 9455.2.
Office Action dated Sep. 16, 2015 received in related U.S. Appl. No. 13/566,012.
Office Action dated Oct. 19, 2015 received in related U.S. Appl. No. 14/168,525.
Office Action dated Oct. 22, 2015 received in related U.S. Appl. No. 14/151,987.
English language abstract only of JP 01-234140 published Sep. 19, 1989.
Notice of Allowance dated Jan. 20, 2015 from related U.S. Appl. No. 13/566,023.
Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0066.4.

(56) References Cited

OTHER PUBLICATIONS

Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Appl. No. 14/169,321.
Extended Supplementary European Search Report dated Mar. 27, 2015 from related European Application No. 12 82 0056.5.
Japanese Office Action dated Jan. 19, 2016 from related Japanese Patent Application No. 2012-036226, together with an English language translation.
Office Action dated Feb. 22, 2016 received in related U.S. Appl. No. 14/168,496.
Office Action dated Mar. 10, 2016 received in related U.S. Appl. No. 13/566,012.
Japanese Office Action dated Apr. 26, 2016 from related Japanese Patent Application No. 2012-157788.
Japanese Office Action dated Apr. 26, 2016 from related Japanese Patent Application No. 2012-154945.
Notice of Allowance dated Apr. 22, 2016 issued in U.S. Appl. No. 14/157,920.
Office Action dated May 9, 2016 received in related U.S. Appl. No. 14/170,856.
European Patent Office Communication dated May 23, 2016 in related European Application No. 12 819 877.7.
Office Action dated Jun. 16, 2016 received in related U.S. Appl. No. 14/169,742.
Japanese Office Action dated Jun. 14, 2016 in related Japanese Patent Application No. 2012-012104.
Japanese Office Action dated Jun. 28, 2016 in related Japanese Patent Application No. 2013-526973.

\* cited by examiner

MEDICAL MANIPULATOR AND SURGICAL SUPPORT APPARATUS

Priority is claimed on Provisional Patent Application No. 61/515,203, filed Aug. 4, 2011, the contents of which are incorporated herein by reference.

BACKGROUND OF THE INVENTION

1. Field of the Invention

The present invention relates to a medical manipulator and a surgical support apparatus.

2. Description of Related Art

Conventionally, various medical manipulators have been investigated in order to perform procedure by remote operation. Examples of this type of medical manipulators are disclosed, for example, in the specifications of U.S. Pat. No. 6,246,200 and U.S. Pat. No. 6,441,577.

By using this type of medical manipulator, when an input apparatus (i.e., an input section) is operated at an operator console, the user, who is generally a surgeon, is able to perform a minimally invasive surgical operation on a patient. By using a trolley system that is placed beside a patient, it is possible to control the movements of endoscopically used surgical instruments using a computer on the operator console.

A typical trolley system is provided with a base section whose external configuration does not change when tissue is being treated, and a drive section that makes articulated movements based on operations input via the operator console. A typical drive section is provided with at least three slave manipulators such as robots in which a plurality of shaft-shaped components are connected by articulated joints. Of the three slave manipulators, the central slave manipulator supports an endoscope, while the slave manipulators on each side support surgical instruments that treat tissue.

SUMMARY OF THE INVENTION

The present invention is a medical manipulator that includes: a holding portion whose proximal end portion is fixed to a base; a positioning portion that has a fixing portion that is fixed to a distal end portion of the holding portion, and that is formed such that a treatment portion of a surgical instrument is able to move relative to the fixing portion; a reference orientation detecting portion that detects an orientation of a reference position on the positioning portion; a drive section that is used to move the treatment portion relative to the fixing portion; and a displacement detecting section that detects an amount of movement, including angular displacement, of the treatment portion relative to the reference position, and that calculates as the orientation on the treatment portion an orientation that is different by an amount of angular displacement that it has itself detected from the orientation on the reference position detected by the reference orientation detecting portion.

DETAILED DESCRIPTION OF THE INVENTION

First Embodiment

Hereinafter, a first embodiment of the surgical support apparatus according to the present invention will be described with reference made to FIG. 1 through FIG. 7.

Figure 1:
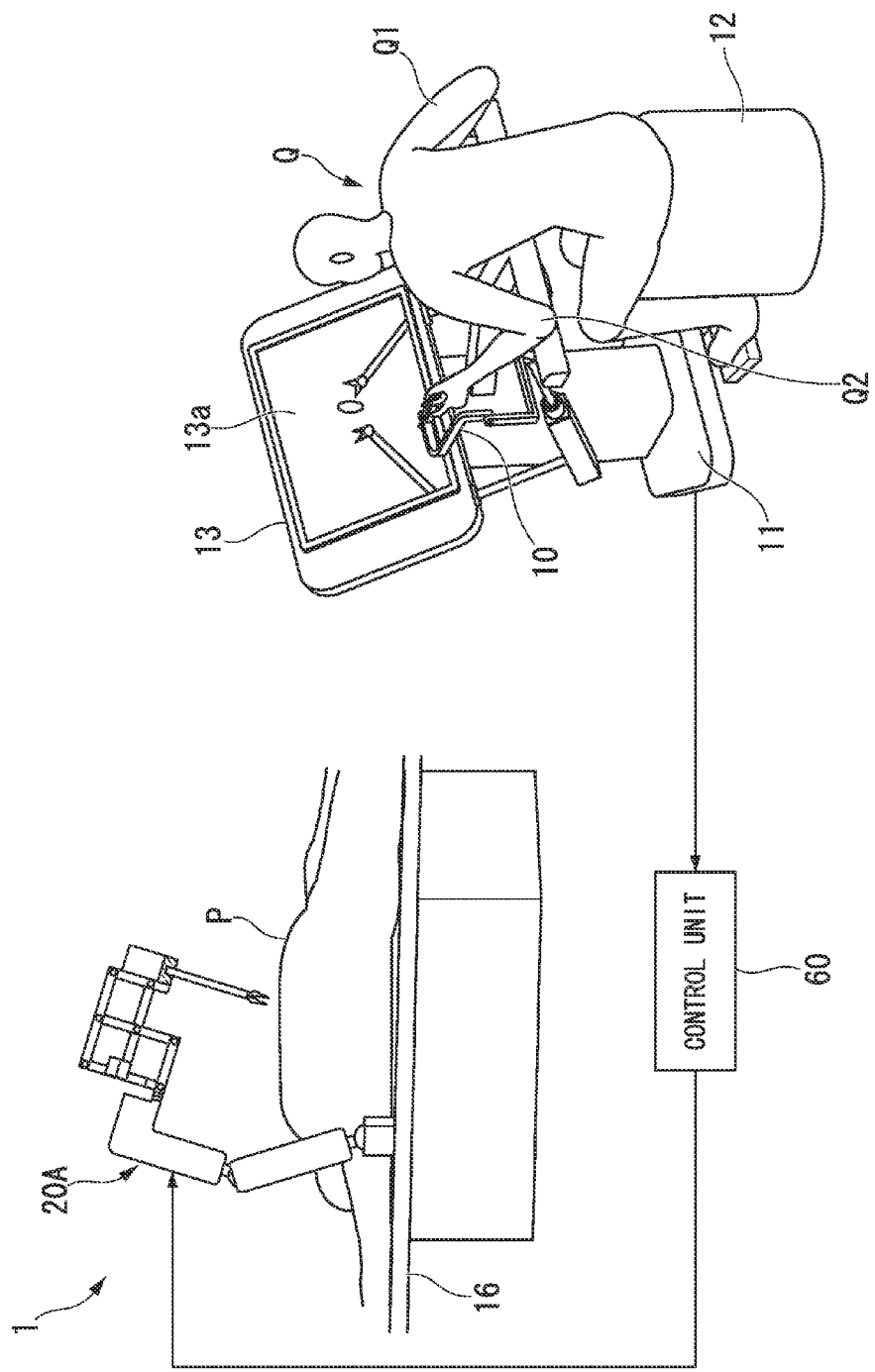
FIG. 1 is an overall view of a surgical support apparatus of a first embodiment of the present invention.
Figure 2:
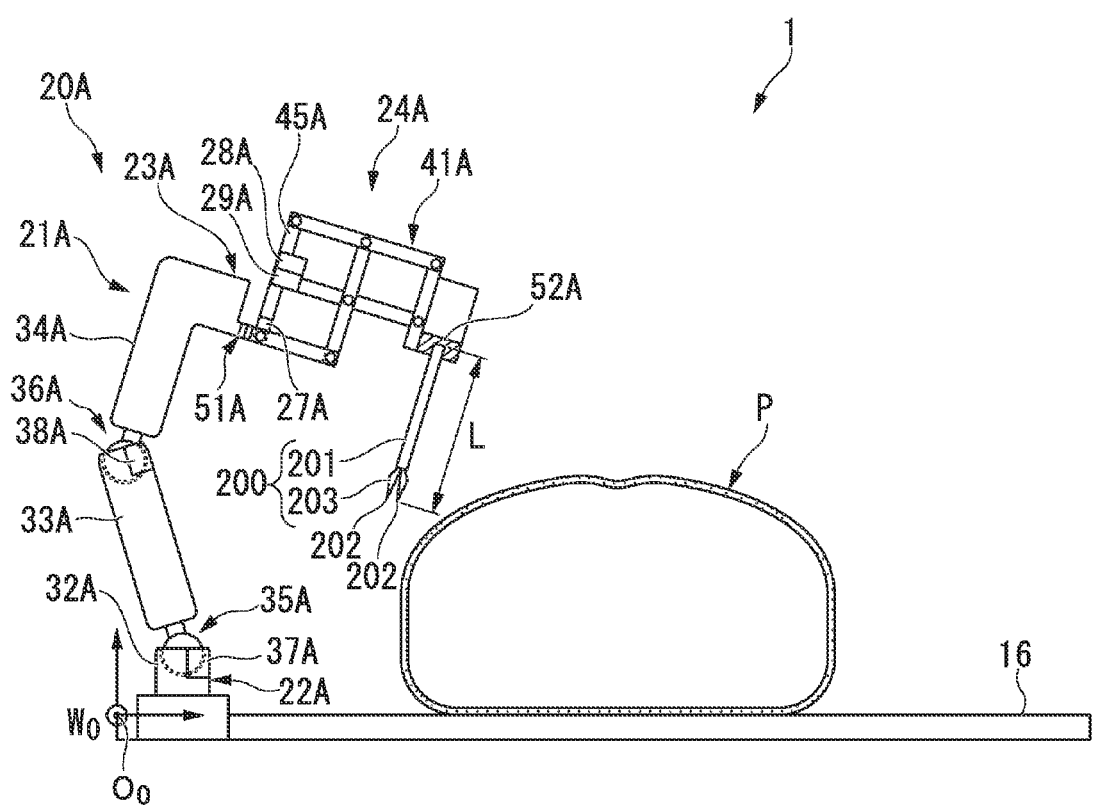
FIG. 2 is a side view of a slave manipulator in the same surgical support apparatus.

As is shown in FIG. 1, a surgical support apparatus 1 of the present embodiment is provided with a master manipulator (i.e., input section) 10, a display unit 13, one slave manipulator of the present invention (i.e., medical manipulator) 20A, and a control unit 60. The surgical support apparatus 1 is constructed such that, as is shown in FIG. 2, a known rigid treatment instrument can be removably attached thereto as a surgical instrument 200.

Hereinafter, firstly, the surgical instrument 200 will be described.

The structure of the surgical instrument 200 is not particularly restricted, however, in the present embodiment, forceps are used. As is shown in FIG. 2, the surgical instrument 200 is an instrument in which a forceps portion (i.e., a treatment portion) 203 that is formed by a pair of forcep pieces 202 is provided at a distal end portion of a surgical instrument insertion portion 201 that is formed in a cylindrical shape out of a hard material such as stainless steel or the like. The respective forcep pieces 202 are turnably supported by a pin (not shown) that is provided at a distal end portion of the surgical instrument insertion portion 201. An operating wire (not shown) is inserted inside the surgical instrument insertion portion 201 such that it is able to advance and retract. A distal end portion of the operating wire is connected to the forcep pieces 202, and a proximal end portion of the operating wire extends to a proximal end side of the surgical instrument insertion portion 201. A wire operating motor (not shown) is incorporated inside the proximal end portion of the surgical instrument insertion portion 201. The proximal end portion of the operating wire is connected to a rotation shaft of the wire operating motor, and by driving the wire operating motor, the operating wire can be advanced or retracted relative to the surgical instrument insertion portion 201 so as to cause the pair of forceps pieces 202 to either move away from each other or come close to each other, namely, to either open or close.

Electrical contact points of the wire operating motor are exposed to the outside via the proximal end portion of the surgical instrument insertion portion 201.

The length in the longitudinal direction of the surgical instrument insertion portion 201 of the surgical instrument 200 is set to L.

Next, the various component elements of the surgical support apparatus 1 will be described.

A manipulator having a known structure can be used as the master manipulator 10, and in the present embodiment, a pair of master manipulators 10 (only one master manipulator 10 can be seen in the drawing) are provided on a support pedestal 11, as is shown in FIG. 1. While seated on a chair 12, a user Q such as a surgeon operates one of the pair of master manipulators 10 using his right hand Q1, and operates the other using his left hand Q2. Based on the operation (i.e. the input) performed by the user Q, the master manipulator 10 is able to send signals that form operating commands. These operating commands are described below, however, commands relating to the position and orientation of the forceps portion 203 are included in the operating commands.

The display unit 13, which has a display panel 13a such as a liquid crystal panel or the like, is fixed to an upper portion of the support pedestal 11. Image signals obtained by converting images acquired by an observation section of an endoscope 56 (described below) into signals are processed by the control unit 60, and the processed images can then be displayed on the display unit 13.

Figure 3:
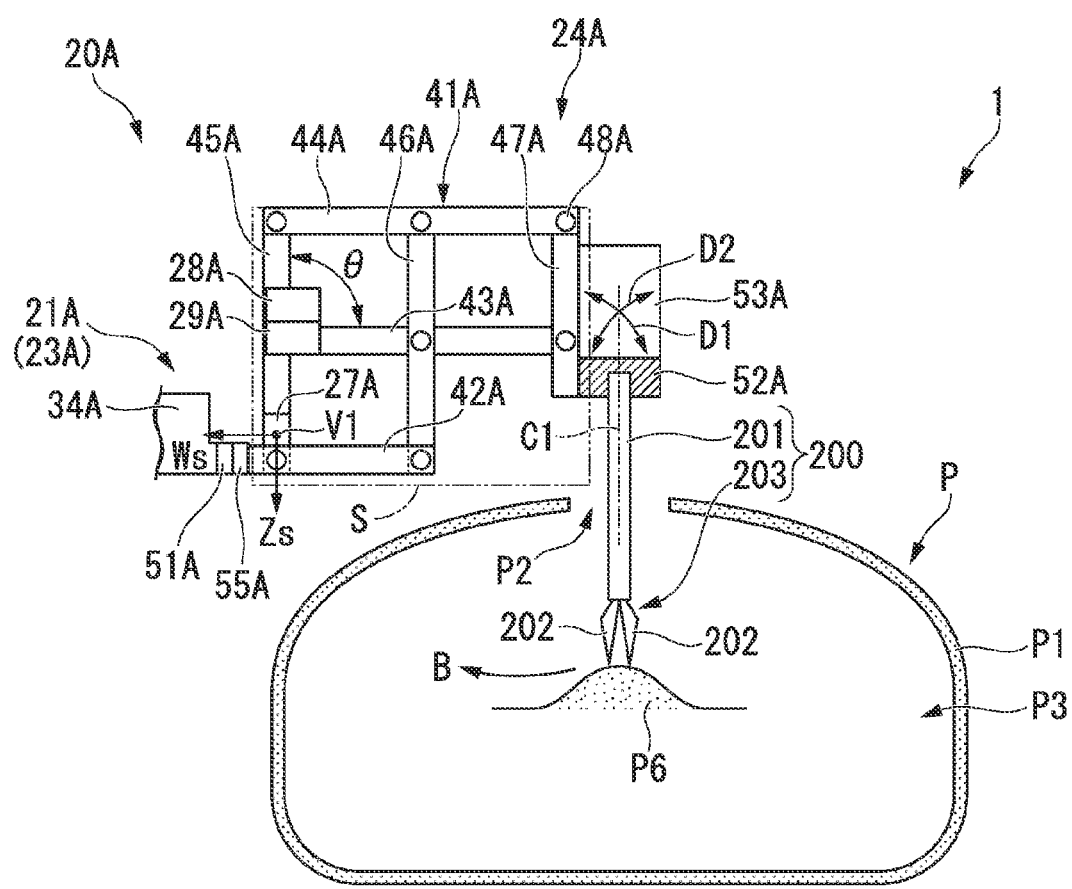
FIG. 3 is a pattern diagram showing a side view of a positioning arm of the same slave manipulator when an angle θ is approximately 90°.

As is shown in FIG. 2 and FIG. 3, the slave manipulator 20A has a slave arm (a holding portion) 21A whose proximal end portion 22A is fixed to a surgery top board (a base) 16, a positioning arm (a positioning portion) 24A that is fixed to a distal end portion 23A of the slave arm 21A, an orientation sensor (a reference orientation detecting portion) 27A, a removable portion drive section 28A, and a removable position detecting section 29A that are provided on the positioning arm 24A, a treatment portion initial position detecting section 30A in which the position and orientation in the initial state of the forceps portion 203 of the surgical instrument 200 that has been removable portion 52A (described below) are stored, and a treatment portion position detecting section 31A in which the position and orientation of the forceps portion 203 are calculated and stored.

Note that, in the following description, structure of the slave manipulator 20A is indicated by attaching the character A after a numerical digit.

As is shown in FIG. 2, the slave arm 21A is constructed by connecting together a stand 32A and two shaft bodies 33A and 34A using commonly known ball joints 35A and 36A. Specifically, the stand 32A and the shaft body 33A are connected together by the ball joint 35A, while the shaft body 33A and the shaft body 34A are connected together by the ball joint 36A. The stand 32A is fixed to the surgery top board 16. Note that the stand 32A forms the proximal end portion 22A of the slave arm 21A, and a distal end portion of the shaft body 34A forms the distal end portion 23A of the slave arm 21A.

The shaft body 33A can be made to swing relative to the stand 32A via the ball joint 35A. The shaft body 34A can be made to swing relative to the shaft body 33A via the ball joint 36A.

A fixing mechanism 37A is provided in the ball joint 35A, and the ball can be fixed in the bearing that forms part of the ball joint 35A by means of this fixing mechanism 37A. This structure enables the shaft body 33A to be fixed to the stand 32A.

In the same way, a fixing mechanism 38A is provided in the ball joint 36A, and the shaft body 34A is able to be fixed to the shaft body 33A.

When the fixing provided by the fixing mechanisms 37A and 38A is released, the slave arm 21A, which is formed in the manner described above, is placed in an adjustment mode in which the positions of the shaft bodies 33A and 34A relative to the stand 32A are able to be adjusted. In contrast, when the fixing provided by the fixing mechanisms 37A and 38A is performed, the slave arm 21A is placed in a fixed mode in which the positions of the shaft bodies 33A and 34A relative to the stand 32A are fixed.

The slave arm 21A is able to be switched between the adjustment mode and the fixed mode.

The positioning arm 24A is provided with what is known as a parallel link 41A. Specifically, as is shown in FIG. 3, the parallel link 41A has first side elements 42A, 43A, and 44A that are placed in parallel with each other, and second side elements 45A, 46A, and 47A that are placed in parallel with each other. The first side elements 42A, 43A, and 44A and the second side elements 45A, 46A, and 47A are formed in a bar shape from a metal such as stainless steel or the like. In this example, the length of the first side elements 43A and 44A are set the same as each other, while the first side element 42A is set shorter than the first side element 43A. The first side element 43A is placed between, and in parallel with, the first side element 42A and the first side element 44A.

The lengths of the second side elements 45A and 46A are set the same as each other, while the second side element 47A is set shorter than the second side element 45A. The second side element 46A is placed between, and in parallel with, the second side element 45A and the second side element 47A.

The second side elements 45A, 46A, and 47A are supported by pins 48A, which are provided in the first side element 44A, such that they are able to turn on a reference plane S relative to the first side element 44A.

In the same way, the second side elements 45A, 46A, and 47A are supported by the pins 48A that are provided in the first side element 43A such that they are able to pivot on the reference plane S relative to the first side element 43A. The second side elements 45A and 46A are supported by the pins 48A that are provided in the first side element 42A such that they are able to turn on the reference plane S relative to the first side element 42A.

A turning mechanism 55A that supports a distal end side of the first side element 42A, and that enables the first side element 42A to turn on a plane that is orthogonal to the reference plane S is provided. A fixing portion 51A that fixes the turning mechanism 55A is provided. The positioning arm 24A is fixed in position relative to the slave arm 21A by the fixing portion 51A. Specifically, the fixing portion 51A is fixed to the distal end portion 23A of the slave arm 21A, namely, to the distal end portion of the shaft body 34A. The shaft body 34A of the slave arm 21A and the fixing portion 51A are fixed together by screws or by welding or the like.

By employing the above described structures, the positioning arm 24A can be made to swing relative to the fixing portion 51A in a direction D1 (on the reference plane S) and in a direction D2 (on a plane that is orthogonal to the reference plane S) that are mutually orthogonal to each other.

A removable portion 52A to which a proximal end portion of the surgical instrument insertion portion 201 of the surgical instrument 200 can be removably attached is mounted via a removable portion moving mechanism (treatment portion drive section) 53A to the second arm element 47A. Note that a drive section is formed by this removable portion moving mechanism 53A and the above-described removable portion drive section 28A.

Figure 4:
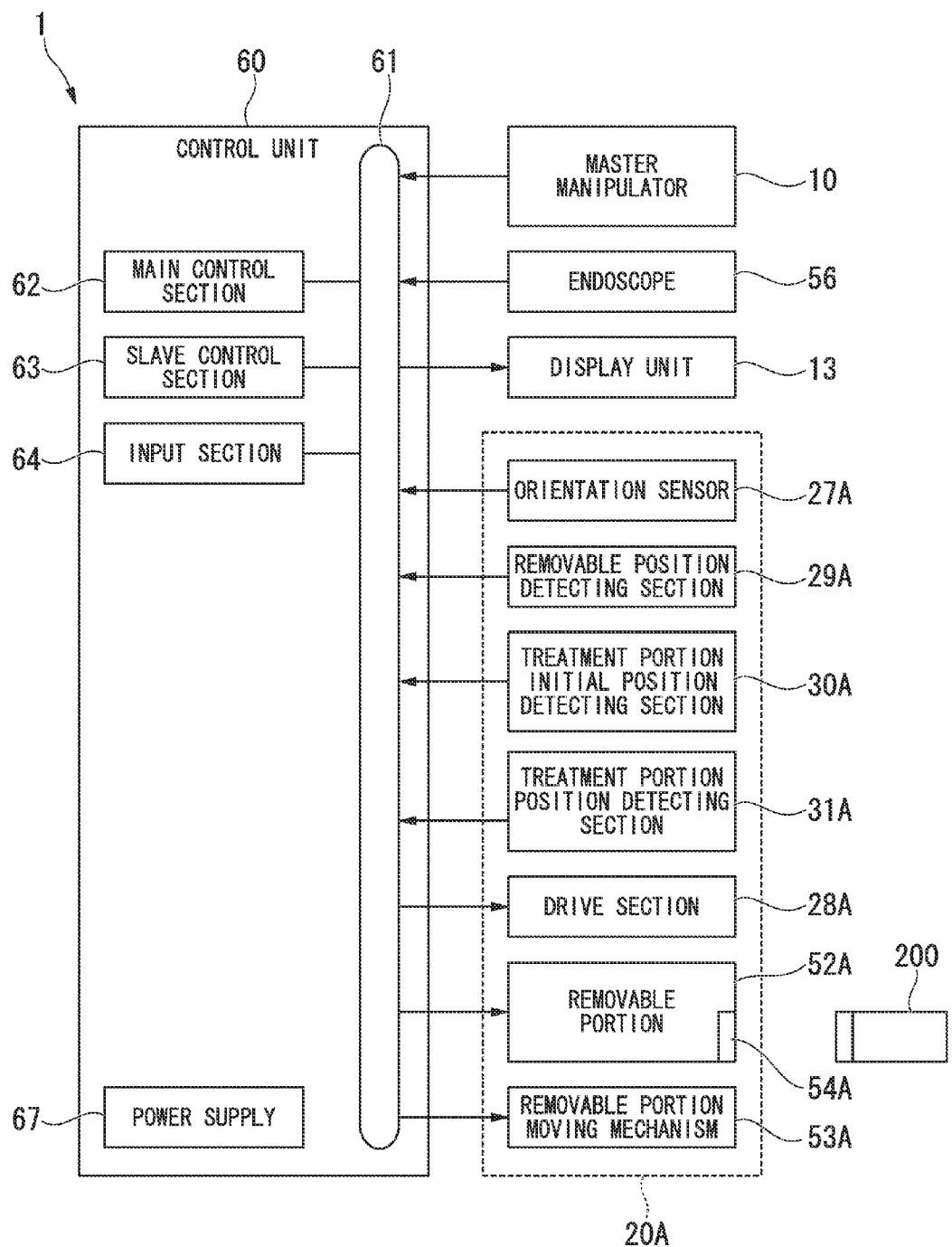
FIG. 4 is a block diagram of the same surgical support apparatus.

As is shown in FIG. 4, when the surgical instrument 200 has been attached to the removable portion 52A, a removable portion-side electrical contact point 54A, which is able to be electrically connected to the electrical contact point of the wire operating motor of the surgical instrument 200, is provided in the removable portion 52A such that it is exposed to the outside.

The removable portion-side electrical contact point 54A is connected to the control unit 60.

As is shown in FIG. 3, the removable portion moving mechanism 53A has a known structure that is able to move the removable portion 52A. In this example, a structure is employed in which, when the surgical instrument 200 has been attached to the removable portion 52A, the surgical instrument insertion portion 201 of the surgical instrument 200 is parallel to the second side element 47A.

The removable portion moving mechanism 53A is able to move the removable portion 52A around a placement central position that is set on a reference axis C1. Specifically, the removable portion moving mechanism 53A is able to move the surgical instrument 200, which has been attached to the removable portion 52A, from the placement central position both advances and retracts in the direction of the reference axis C1, and to also turn it around this reference axis C1 relative to the removable portion 52A.

In the present embodiment, although omitted from the drawings, the orientation sensor 27A has a commonly known gyroscope, and a reference orientation calculating substrate that processes detection results from the gyroscope so as to detect the orientation (direction) of the gyroscope. The orientation of the gyroscope is expressed as, for example, rotation angles around the respective axes of a global coordinate system $W_0$, which is an orthogonal coordinate system in which an original point $O_0$ is prescribed on the top surface of the surgery top board 16 shown in FIG. 2.

As is shown in FIG. 3, the orientation sensor 27A is mounted in the longitudinal direction of the second side element 45A of the positioning arm 24A. Namely, in this example, a reference position V1, where the orientation sensor 27A detects the orientation, is set on the second side element 45A, in other words, is set on the proximal end portion of the positioning arm 24A. The orientation sensor 27A is able to detect the orientation in the longitudinal direction of the second side element 45A at the reference position V1.

At this time, because a structure is employed in which the surgical instrument 200 is parallel to the second side element 45A, the orientation of the longitudinal direction of the second side element 45A at the reference position V1 of the second side element 45A substantially coincides with the orientation of the insertion direction of the surgical instrument 200.

As is shown in FIG. 4, the orientation of the reference position V1, which is detected by the orientation sensor 27A, is transmitted to the control unit 60.

The removable portion drive section 28A has a motor and gears (not shown). By driving the motor so that the gears are rotated, an angle θ between the first side element 43A and the second side element 45A shown in FIG. 3 can be adjusted from an acute angle to an obtuse angle.

Figure 5:
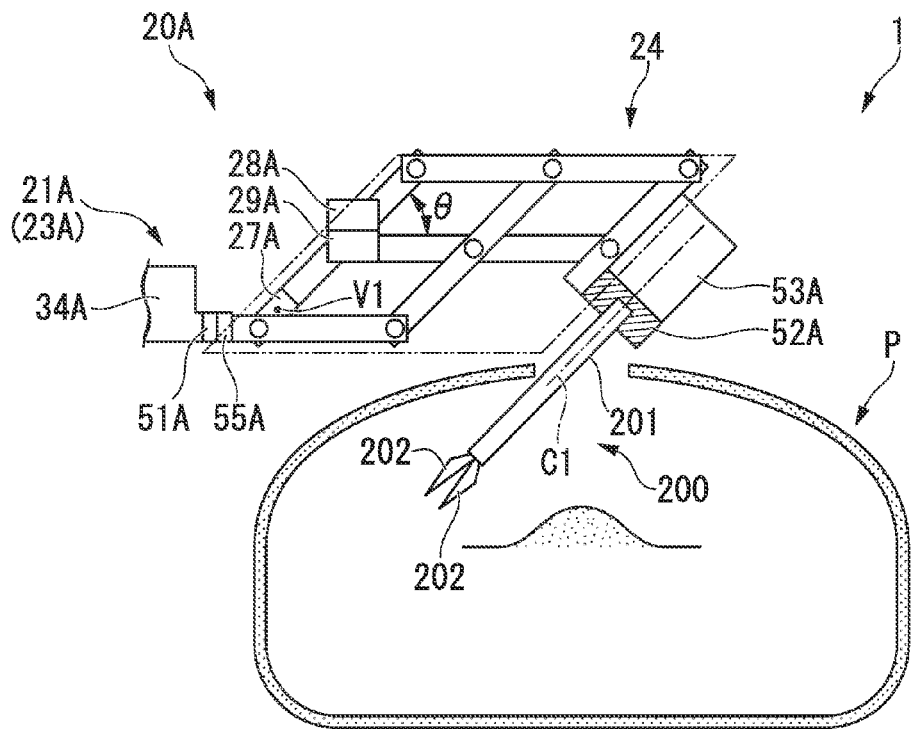
FIG. 5 is a pattern diagram showing a side view of a positioning arm of the same slave manipulator when the angle θ is an acute angle.

Because the positioning arm 24A has the above-described structure, once the angle θ has been determined, the shape of the positioning arm 24A is also uniquely determined. In FIG. 3, a state in which the angle θ is approximately 90° is shown, however, if, as is shown in FIG. 5, the removable portion drive section 28A is driven so that the angle θ changes to an acute angle, then the position and orientation of the removable portion 52A relative to the fixing position 51A can be moved.

Although omitted from the drawings, the removable position detecting section 29A has an angle detecting sensor such as an encoder or the like that detects the above-described angle θ, and a removable position calculating substrate that detects the position (the distance) and orientation (the angle) of the removable portion 52A relative to the reference position V1 from the detected angle θ. The removable position calculating substrate is provided with calculating elements, memory, and a timer (not shown).

The distances between adjacent pins 48A, the position on the second side element 45A where the reference position V1 has been set, and the position on the second side element 47A where the removable portion 52A has been attached and the like are stored in the memory.

The calculating elements are able to calculate the distance (the position) from the reference position V1 to the removable portion 52A, as well as the angle (the orientation) from the respective distance information stored in the memory and from the angle θ detected by the angle detecting sensor.

Moreover, the calculating elements detect the distances and angles from the reference position V1 to the removable portion 52A at respective unit times that have been set in the timer, and the detected distance and angle information is stored in the memory as the position and orientation of the removable portion 52A. The unit times are set in accordance with the processing speed of the control unit 60 as well as with the content of the procedure between approximately, for example, 1 ms (milliseconds) and 500 ms.

The calculating elements calculate the amount of change in position and the amount of change in orientation per unit time of the removable portion 52A relative to the reference position V1 from the position and orientation of the removable portion 52A at each of the unit times that have been stored in the memory.

The above-described position and orientation of the removable portion 52A relative to the reference position V1, which were calculated by the removable position detecting section 29A, as well as the amount of change in position and the amount of change in orientation of the removable portion 52A are transmitted to the control unit 60 (see FIG. 4).

The length L of the surgical instrument 200 and the like have been stored in advance in the treatment portion position detecting section 31A, and this treatment portion position detecting section 31A calculates the position and orientation of the forceps portion 203 relative to the removable portion 52A. In this example, the position of the forceps portion 203 relative to the position of the proximal end portion of the surgical instrument insertion portion 201 is a position that is separated therefrom in the longitudinal direction of the surgical instrument insertion portion 201 by the length L.

Note that a displacement detecting section is formed by this treatment portion position detecting section 31A and the above-described removable position detecting section 29A.

The treatment portion position detecting section 31A calculates as the position and orientation of the forceps portion 203 a position and orientation attained when it is moved from the initial position of the reference position V1 and from the orientation detected by the orientation sensor 27A by the movement distance and angle of the removable portion 52A, which are detected by the detection position detecting section 29A, and also by the position and orientation of the forceps 203 relative to the removable portion 52A.

Specifically, the calculating element calculates the distance from the reference position V1 (the original point) to the removable portion 52A, which was detected by the removable position detecting section 29A, relative to any one of the axes (for example, the $Z_s$ axis) that constitutes a local coordinate system $W_s$, which is an orthogonal coordinate system whose original point has been prescribed as the initial position of the reference position V1 and that faces in the direction of the longitudinal axis of the second side element 45A, as the position on that particular axis of the removable portion 52A. Furthermore, it is also calculated as a position separated, on that axis, from the position of the removable portion 52A by the distance from the removable portion 52A to the position of the forceps portion 203.

The calculation of this position is performed in the same way for the remaining two axes that constitutes the local coordinate system $W_s$.

On the other hand, in the calculation of the orientation of the forceps portion 203, for any particular one of the axes constitutes a global coordinate system $W_0$, by adding the rotation angle around that axis of the removable portion 52A, which has been detected by the removable position detecting section 29A, to the rotation angle around that axis at the reference position V1, the rotation angle (the orientation) around that axis of the removable portion 52A is calculated. Furthermore, an orientation attained by moving from the orientation of the removable portion 52A by the orientation of the forceps 203 relative to the removable portion 52A is calculated as the orientation of the forceps portion 203.

This calculation of the rotation angle based on summing, namely, the calculation of the orientation is performed in the same way for the remaining two axes constitute the global coordinate system $W_0$.

The position and orientation of the forceps portion 203 in the initial state that have been calculated by the treatment portion position detecting section 31A are stored in the treatment portion initial position detecting section 30A.

As is shown in FIG. 4, the control unit 60 has a main control section 62 that is connected to a bus 61, a slave control section (a drive section control section) 63, an input section 64, and a power supply 67.

To the bus 61 are connected via metal wiring a commonly-known endoscope 56, as well as the above-described master manipulator 10, display unit 13, orientation sensor 27A, removable position detecting section 29A, treatment portion initial position detecting section 30A, treatment portion position detecting section 31A, removable portion drive section 28A, removable portion 52A, and removable portion moving mechanism 53A.

The main control section 62 and the slave control section 63 are each formed by a CPU (Central Processing Unit), and by control programs and the like.

The slave control section 63 controls the removable portion drive section 28A and the removable portion moving mechanism 53A based on the aforementioned operating commands. The control method is described below.

The main control section 62 performs the general processing for the control unit 60 such as processing signals that are obtained by converting images acquired by an observation section having a CCD (Charge Coupled Device) in the endoscope 56 into image signals, and then transmitting these image signals to the display unit 13.

The input section 64 is, for example, a keyboard, and an assistant inputs required commands thereon. The input commands are transmitted to the main control section 62 and the like.

The power supply 67 supplies power to the respective structures of the master manipulator 10, the endoscope 56, the display unit 13, the slave manipulator 20A, and the control unit 60.

Next, procedures performed using the surgical support apparatus 1 of the present embodiment, which is constructed in the manner described above, will be described focusing on the operations of the slave manipulator 20A and the control unit 60. Hereinafter, an example is described in which the surgical instrument 200 is introduced into the body cavity of a patient and subject tissue is then treated.

When the surgical support apparatus 1 is activated, power is supplied from the power supply 67 of the control unit 60 to the master manipulator 10 and the slave manipulator 20A and the like. At this point, the slave arm 21A is in fixed mode.

As is shown in FIG. 1 and FIG. 2, an assistant then causes a patient P to lie on the surgery top board 16 and performs the necessary treatment. Using a knife or the like (not shown), an incision is made in the body wall P1 of the patient P, as is shown in FIG. 3, so as to form an aperture P2. A trocar (not shown) is then placed at this aperture P2.

Based on commands made by the user Q, the proximal end portion of the surgical instrument insertion portion 201 of the surgical instrument 200 is then attached to the removable portion 52A. The endoscope 56 is then introduced through a separate aperture that has been formed in the body wall P1, and treatment is performed while the user confirms the images acquired by the observation section displayed on the display unit 13.

The slave arm 21A is then switched to adjustment mode, and the shaped of the slave arm 21A is then distorted such that the forceps portion 203 of the surgical instrument 200 is introduced into the interior of the body cavity P3 of the patient P through the aperture P2. At this time, the surgical instrument 200 extends downwards, and the angle θ of the positioning arm 24A is approximately 90°.

After the surgical instrument 200 has been positioned in this manner, the slave arm 21A is switched to fixed mode.

The input section 64 is then operated so that the rotation angle of the forceps portion 203, which is obtained by adding together the rotation angles detected by the orientation sensor 27A, the removable position detecting section 29A, and the treatment portion position detecting section 31A, is stored (initialized) in the treatment portion initial position detecting section 30A as the initial orientation of the forceps portion 203. The position of the forceps portion 203 when the initial position of the reference position V1 was taken as a virtual original point is then stored as the initial position of the forceps portion 203 in the treatment portion initial position detecting section 30A.

The treatment portion initial position detecting section 30A then transmits the stored initial position and initial orientation of the forceps portion 203 to the slave control section 63.

Next, the user Q then sits in the chair 12, and operates a pair of master manipulators 10 by gripping them respectively with their right hand Q1 and their left hand Q2. Here, a case is described in which the user Q drives the removable portion drive section 28A by operating the master manipulators 10, so as to swing the surgical instrument 200 and change the position of the forceps portion 203 in a horizontal direction.

Hereinafter, in order to simplify the description, only the position of the forceps portion 203 is concentrated on in this description.

Figure 6:
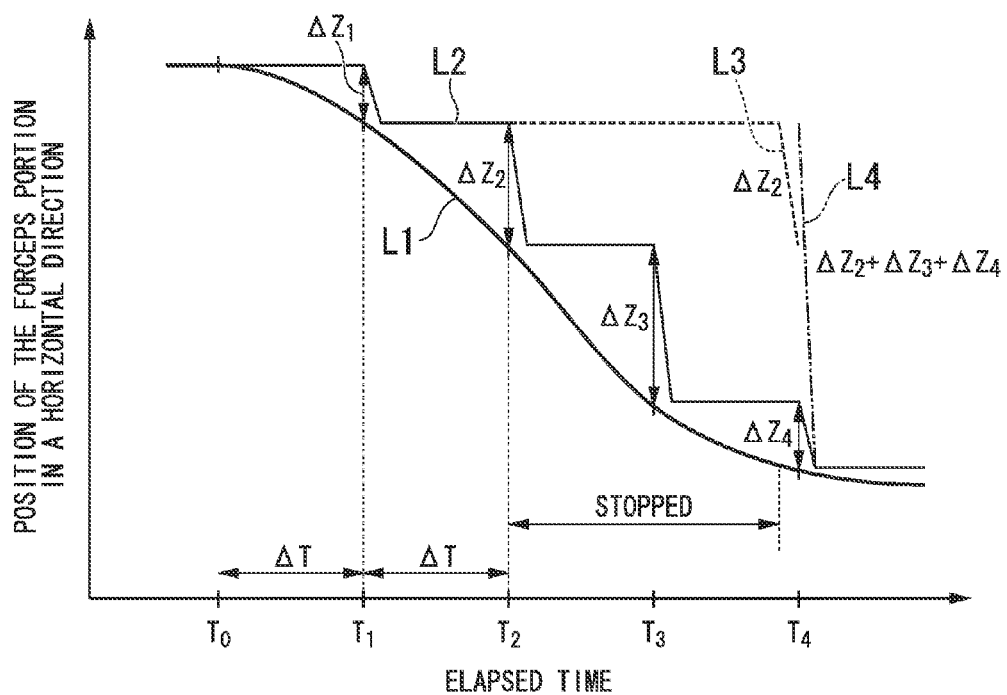
FIG. 6 is a view showing changes over time between the position set by an operating command and the position of a forceps portion.
Figure 7:
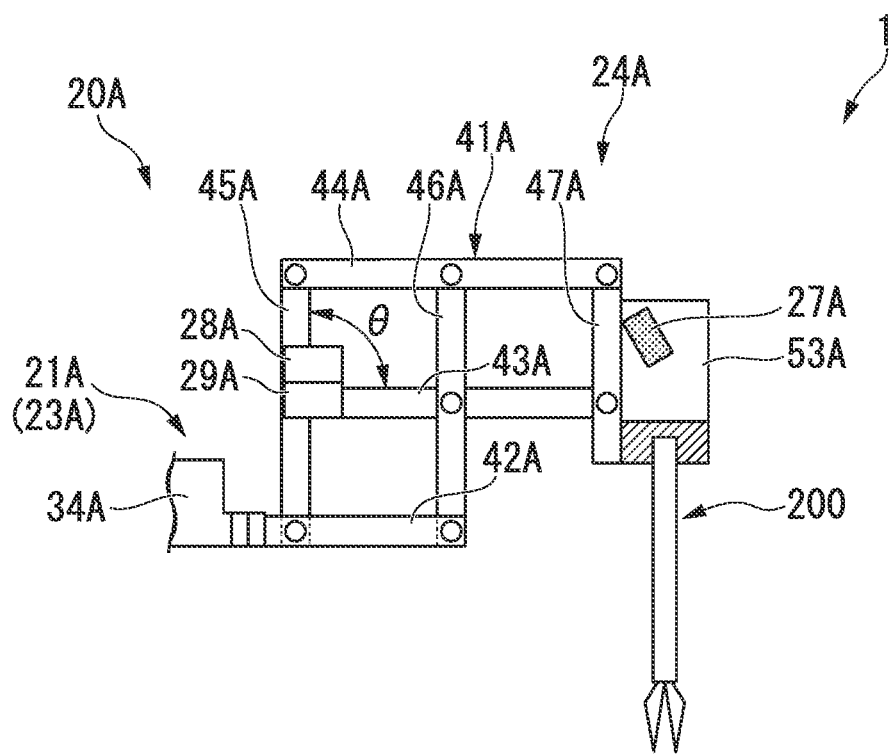
FIG. 7 is a side view of a positioning arm in a modified example of the same slave manipulator.

In FIG. 6, the curve L1 shows the position in the horizontal direction of the forceps portion 203 that is based on the operating commands (the target value), while the curve L2 shows the position of the forceps portion 203 as recognized by the control unit 60 (the measured value).

It will be assumed that the user Q has operated the master manipulator 10 from an operation start time $T_0$, and, as is shown on the curve L1, has issued an operating command to cause the forceps portion 203 of the surgical instrument 200 to move in the direction shown by the arrow B in FIG. 3.

Firstly, in a target change amount calculation step, the slave control section 63 calculates an amount of change in a target position $\Delta Z_1$ per unit time $\Delta T$ from the operation start time $T_0$ to the time $T_1$ for the forceps portion 203 shown by the operating command, at the time $T_1$ when a time unit $\Delta T$ has passed from the operation start time $T_0$.

Next, in a moving step, the slave control section 63 controls the removable portion drive section 28A such that the forceps portion 203 moves by the amount of change in the target position $\Delta Z_1$ per unit time $\Delta T$, namely, such that the amount of change from the initial position of the forceps portion 203 that was stored at initialization is $\Delta Z_1$. Specifically, the removable portion drive section 28A is controlled such that the angle θ at the time $T_1$ is reduced (see FIG. 5).

Next, in the target change amount calculation step, the slave control section 63 calculates an amount of change in a target position $\Delta Z_2$ per unit time $\Delta T$ from the operation start time $T_1$ to the time $T_2$ for the forceps portion 203 shown by the operating command, at the time $T_2$ when a time unit $\Delta T$ has passed from the time $T_1$.

Next, in the moving step, the slave control section 63 controls the removable portion drive section 28A such that the forceps portion 203 moves by the amount of change in the target position $\Delta Z_2$ per unit time $\Delta T$, namely, such that the amount of change from the position of the forceps portion 203 at the time $T_1$ is $\Delta Z_2$. Specifically, the removable portion drive section 28A is controlled such that the angle θ at the time $T_2$ is reduced.

In this manner, a combination of the target change amount calculation step and the moving step is repeated a desired number of times, so that the forceps portion 203 is swung in the manner shown by the arrow B in FIG. 3 in the sequence of the amount of change $\Delta Z_3$, the amount of change $\Delta Z_4$, . . . and so on. The number of times this combination of steps is repeated may be one time or may be two or more times.

Note that, as is described above, because the surgical instrument 200 is attached to the parallel link 41A, when the intersection point between the first side element 42A and these surgical instrument 200, which is attached to the removable portion 52A is set as a steady point (the port position), then the surgical instrument 200 is placed on this steady point irrespective of the angle θ of the parallel link 41A. Namely, by moving the slave manipulator 20A such that the aperture portion P2 in the patient P coincides with the steady point, the surgical instrument 200 passes through the aperture P2 irrespective of the angle θ of the parallel link 41A.

Moreover, a case might also be considered in which, for example, due to an interruption in the power supply 67 or the like, the operation of the surgical support apparatus 1 may abruptly stop while the master manipulator 10 is being operated and the surgical instrument 200 is being swung in this manner.

For example, as is shown in FIG. 6, a case in which operations of the surgical support apparatus 1 have been abruptly stopped immediately prior to the forceps portion 203 being moved by the amount of change $\Delta Z_2$ may be assumed. In this case, because the movement of the forceps portion 203 is controlled using amounts of change, when the power supply 67 is restored and the operations of the surgical support apparatus 1 are restarted, the forceps portion 203 attempt to move by the amount of change $\Delta Z_2$, as is shown by the curve L3.

In contrast, unlike the present invention, when the forceps portion 203 is controlled using target positions, when the operations of the surgical support apparatus are restarted, the forceps portion attempts to move to the target position that was in effect when the operations of the surgical support apparatus were restarted, as is shown by the curve L4, and there is a possibility that the forceps portion will move a considerable distance, for example, by a value obtained using the formula ($\Delta Z_2 + \Delta Z_3 + \Delta Z_4$)

Here, only the position of the forceps portion 203 has been described, however, the above description also applies to the orientation of the forceps portion 203.

The description will now return to the procedures performed using the surgical support apparatus 1.

The user Q then swings the surgical instrument 200 via the removable portion drive section 28A by operating the master manipulators 10, and, as is shown in FIG. 3, causes the forceps portion 203 to opposite a lesion portion P6, which is the treatment subject, inside the body cavity P3. The removable portion 52A to which the surgical instrument 200 has been attached is then pushed down via the removable portion moving mechanism 53A so that the forceps portion 203 is brought into contact with the lesion portion P6. If necessary, the surgical instrument 200 can be turned around the reference axis C1 via the removable portion moving mechanism 53A.

Power is then supplied to the wire operating motor of the surgical instrument 200 via the removable portion 52A, so that the pair of forceps pieces 202 close and grip the lesion portion P6.

Thereafter, the appropriate treatment is performed on the lesion portion P6 and the series of procedures is ended.

In the slave manipulator of the medical manipulator described in the specifications of U.S. Pat. Nos. 6,246,200 and 6,441,577, generally, a brake system and an angle sensor are placed in each joint, and a removable portion to which a surgical instrument can be attached is provided on the slave manipulator. In addition, based on the angle information for each joint, the position and orientation (the direction) of the removable portion of the slave manipulator and, furthermore, the position and orientation of the distal end portion of the surgical instrument are calculated.

In this case, in order to obtain the absolute position and orientation of the distal end portion (the treatment portion)

of the surgical instrument, the same number of angle sensors as the number of joints in the slave manipulator are needed, so that the problems arise that, not only does the size of the apparatus increase, but the cost thereof also increases.

In contrast to this, according to the slave manipulator 20A of the present embodiment, the orientation sensor 27A, which is capable of detecting orientation on the global coordinate system $W_0$, is provided in the positioning arm 24A. Because of this, it is possible to detect the position and the orientation of the reference position V1 of the positioning arm 24A without providing an angle detecting sensor in each joint of the slave arm 21A, as is the case conventionally. Furthermore, the orientation of the forceps portion 203 relative to the reference position V1 can be detected by means of a displacement detecting section.

In this way, by providing two sensors, namely, the orientation sensor 27A and the displacement detecting section, it is possible to detect the orientation of the removable portion 52A on the global coordinate system $W_0$. Accordingly, it is possible to decrease the number of sensors required to detect the orientation of the forceps portion 203.

Because the positioning arm 24A is provided with the parallel link 41A, by placing the slave arm 21A in fixed mode when the slave manipulator 20A has been moved such that the aperture P2 of the patient P coincides with the steady point, the surgical instrument 200 is able to through the aperture P2 irrespective of the angle θ of the parallel link 41A.

As a consequence of this, it is possible to prevent the surgical instrument 200 from applying any external force to the edge portions of the aperture P2 irrespective of the angle of swing of the surgical instrument 200.

Because the reference position V1 is set to a point on the second side element 45A of the slave arm 21A, namely, to the proximal end portion of the positioning arm 24A, the reference position V1 does not move after the slave arm 21A has been placed in fixed mode. Because the reference position V1, which forms the original point for the position and orientation of the removable portion 52A that is detected by the removable position detecting section 29A, does not move, the position and orientation of the removable portion 52A can be easily calculated.

The treatment portion position detecting section 31A calculates the position and orientation of the forceps portion 203 from information such as the length L of the surgical instrument 200, which has been stored in advance, and from the calculated position and orientation of the removable portion 52A. Accordingly, it is possible to calculate not only the position and orientation of the removable portion 52A, but to also calculate the position and orientation of the forceps portion 203, which is the actual location where treatment is performed, and it is possible to control accurately.

Moreover, according to the surgical support apparatus 1 of the present embodiment, the slave control section 63 controls the removable portion drive section 28A in accordance with the amount of change in a target position and the amount of change in a target orientation of the removable portion 52A per unit time ΔT, which is expressed as an operating command. Because of this, even if the operations of the surgical support apparatus 1 are brought to a sudden halt, it is possible to prevent the removable portion 52A and the forceps portion 203 of the surgical support apparatus 1 from making large movements when operations are restarted.

Furthermore, by controlling the removable portion drive section 28A in accordance with the amount of change in the target position per unit time ΔT, even if the absolute value positional coordinates of the removable portion 52A in the global coordinate system $W_0$ are unknown, it is possible to control the position of the surgical instrument 200 relatively as it relates to the initial position of the removable portion 52A or to the reference position V1 that was set by the initialization process.

Note that, in the present embodiment, in the initialization process, the position and orientation of the removable portion 52A are stored as the initial position and the initial orientation, however, it is also possible to store the position and orientation of the reference position V1 as the initial position and initial orientation. The reason for this is that, in this case, the same effects as those achieved from the present embodiment can be demonstrated.

In the present embodiment, the removable portion 52A that supports the surgical instrument 200 such that the surgical instrument 200 can be attached thereto or detached therefrom is provided on the positioning arm 24A, however, it is also possible for the positioning arm 24A and the surgical instrument 200 to be formed as a single body so that the surgical instrument 200 and the positioning arm 24A are fixed together. In this case as well, if the position and orientation of the reference position V1 during the initialization process are stored as the initial position and the initial orientation, then the position of the surgical instrument 200 can be controlled relatively to the reference position V1.

In the present embodiment, the removable portion drive section 28A that moves the removable portion 52A is provided on the positioning arm 24A, however, it is also possible to employ a structure in which the removable portion drive section 28A is not provided on the positioning arm 24A, and the removable portion moving mechanism 53A, which only moves the surgical instrument 200, is provided. In this case as well, if the position and orientation of the reference position V1 or the removable portion 52A during the initialization process are stored as the initial position and the initial orientation, then the position of the surgical instrument 200 can be controlled relatively to the initial position.

In the present embodiment, it is also possible to employ a structure in which a plurality of the slave manipulators 20A are provided in the surgical support apparatus 1, and a single orientation sensor 27A is removably attached to the second side element 45A of each slave manipulator 20A. The attaching and detaching between the second side element 45A and the orientation sensor 27A may be a mechanical-type engagement that uses an engaging portion and an engaged portion, or an electromagnetic-type engagement that uses magnets or the like.

As far as a single slave manipulator 20A is concerned, after the slave arm 21A has been placed in fixed mode, then once the position and orientation of the reference position V1 have been detected one time by the orientation sensor 27A, then the orientation sensor 27A becomes unnecessary for that slave manipulator 20A as long as the slave arm 21A remains in fixed mode.

By structuring the orientation sensor 27A in this manner, it is possible to lower the manufacturing costs of the overall surgical support apparatus 1.

In the present embodiment, the orientation sensor 27A is mounted on the second side element 45A of the positioning arm 24A, however, the position where the orientation sensor 27A is mounted is not particularly limited provided that it is able to detect the position and orientation of the reference position V1 on the positioning arm 24A. For example, as in the surgical support apparatus 1 shown in FIG. 7, the orientation sensor 27A may also be mounted on the removable portion moving mechanism 53A. In this case as well, if information about the position where the orientation sensor 27A is mounted on the removable portion moving mechanism 53A is stored in advance in the orientation sensor 27A, then it is able to detect the position and orientation of the reference position on the positioning arm 24A.

Moreover, the orientation sensor 27A may also be mounted on the slave arm 21A. This is because if the positional and attitudinal relationships between the slave arm 21A and the positioning arm 24A are stored in advance in the orientation sensor 27A, then it is able to detect the position and orientation of the reference position on the positioning arm 24A.

The mounting position of the removable position detecting section 29A is not particularly restricted provided that it is able to detect the angle θ formed between any one of the first side elements 42A, 43A, and 44A and any one of the second side elements 45A, 46A, and 47A.

Moreover, in the present embodiment, it is also possible for the reference orientation calculating substrate in the orientation sensor 27A and the removable position calculating substrate in the removable position detecting section 29A to be located within the control unit 60. By employing this type of structure, the control substrates can be integrated, and the structure of the control substrates overall can be made more compact.

It is also possible to employ a structure in which the parallel link 41A is not provided on the first side element 43A and the second side element 46A, but instead the parallel link 41A is only provided on the one pair of first side elements 42A and 44A, and on the one pair of second side elements 45A and 47A.

In the present embodiment, the fixing portion 51A of the positioning arm 24A is fixed to the distal end portion 23A of the slave arm 21A, however, it is also possible to employ a structure in which the fixing portion 51A is removably attached to the distal end portion 23A of the slave arm 21A.

Here, the slave arm deforming step in which the slave arm 21A is deformed to a suitable shape to match the aperture P2 in the patient P, the positioning arm placement step in which the positioning arm 24A is placed such that the steady point in the positioning arm 24A coincides with the aperture P2 in the patient P, and the mounting step in which the fixing portion 51A of the positioning arm 24A is mounted on the distal end portion 23A of the slave arm 21A are prescribed. The sequence in which the slave arm deforming step, the positioning arm placement step, and the mounting step are performed is not particularly restricted, and they may be performed in any desired sequence. After these three steps have been performed, the above-described target change amount calculation step and moving step are repeatedly performed as a combination.

The orientation sensor 27A and the treatment portion initial position detecting section 30A are connected together using wiring. However, it is also possible to employ a structure in which the orientation sensor 27A transmits the detected orientation of the reference position V1 to the treatment portion initial position detecting section 30A by wireless communication.

By employing this type of structure, the size of the slave manipulator 20A can be reduced.

In the present embodiment, in the target change amount calculation step, the slave control section 63 calculates the amount of change in the target position and the amount of change in the target orientation of the treatment portion 203 per unit time ΔT, and, in the moving step, performs control based on this amount of change in the target position and amount of change in the target orientation. However, it is also possible for the slave control section 63 to only calculate one of the amount of change in the target position and the amount of change in the target orientation in the target change amount calculation step, and to perform control in the moving step based on the one calculated amount of change.

Second Embodiment

Next, a second embodiment of the present invention will be described with reference made to FIG. 8 and FIG. 9. Note that the same symbols are used for portions that are the same as those in the above described embodiment, and any description thereof is omitted. Only points of difference therefrom will be described.

Figure 8:
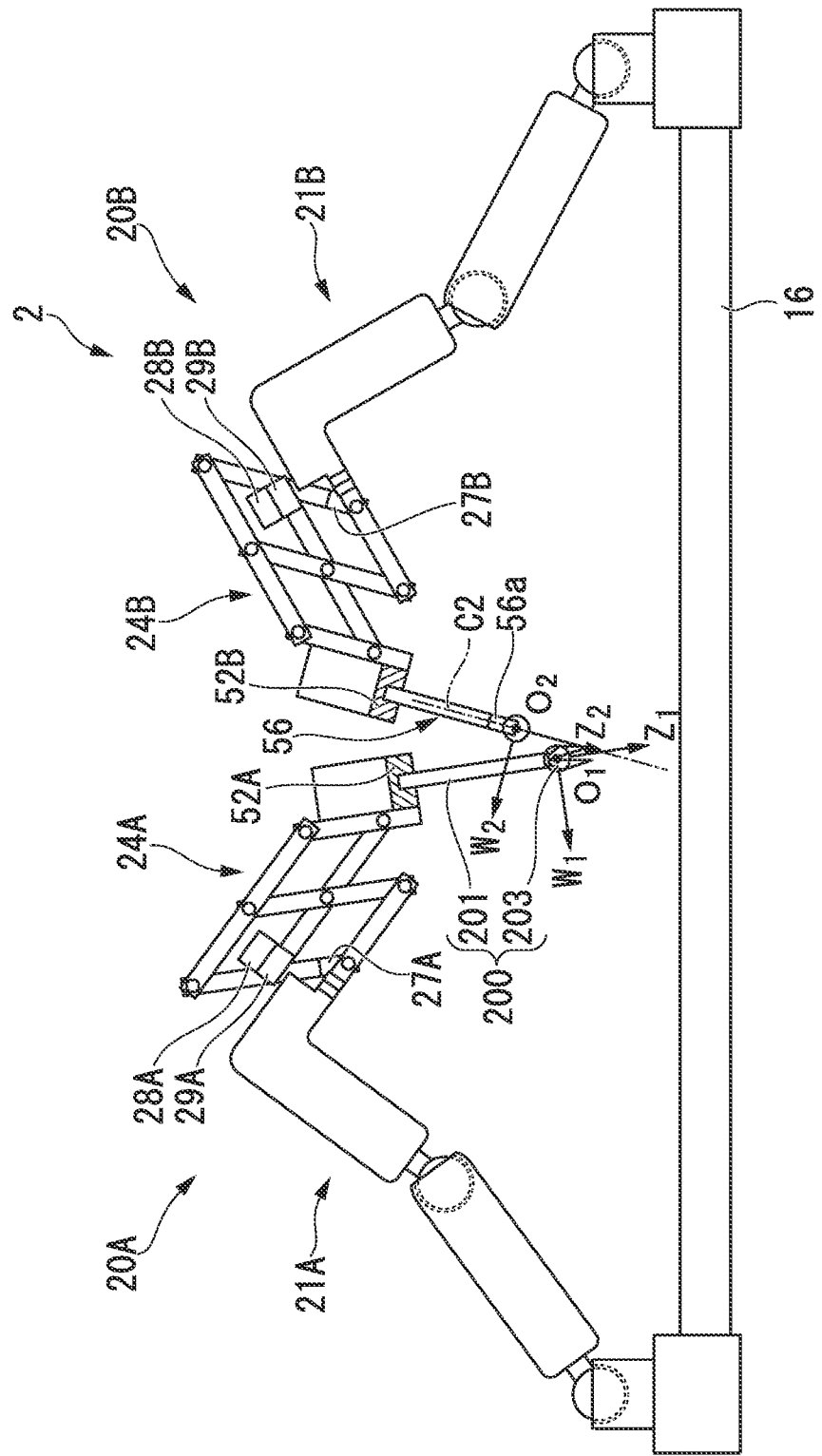
FIG. 8 is a side view of a slave manipulator in a surgical support apparatus of a second embodiment of the present invention.

As is shown in FIG. 8, in a surgical support apparatus 2 of the present embodiment, in addition to the respective component elements of the surgical support apparatus 1 of the first embodiment, there is also provided a slave manipulator 20B of the present invention that has an removable portion 52B to which the above-described endoscope 56 can be removably attached.

Note that because the structure of the slave manipulator 20B is the same as that of the slave manipulator 20A, the structure of the slave manipulator 20B is shown by adding the numerical character 'B' to structure that corresponds to that of the slave manipulator 20A. By doing this, any duplicated description is omitted.

The endoscope 56, in which an observation section 56a that is used to acquire external images along an optical axis C2 is provided, is removably attached to an removable portion 52B that is mounted on a positioning arm 24B.

Figure 9:
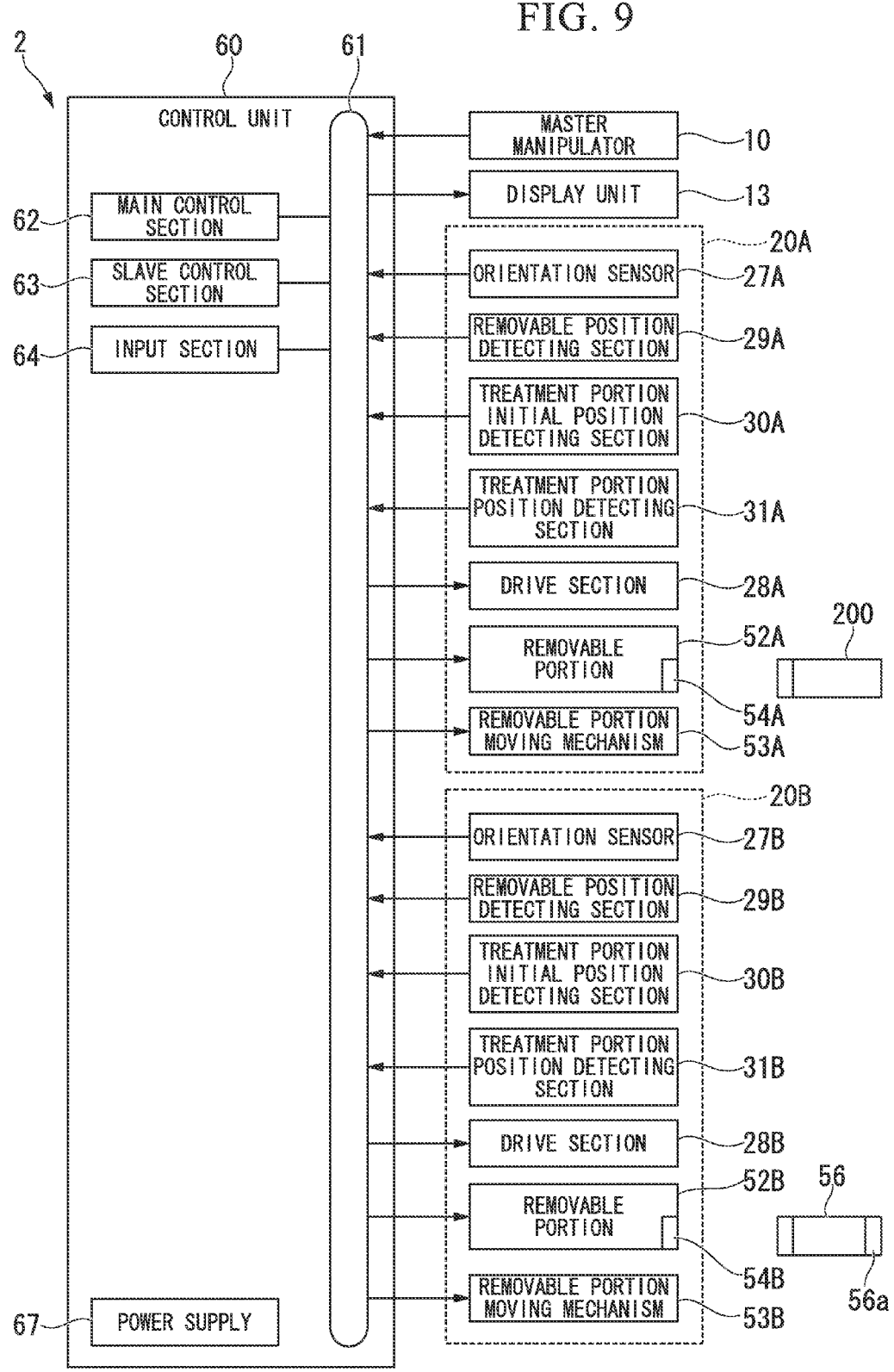
FIG. 9 is a block diagram of the same surgical support apparatus.

When the endoscope 56 has been attached to the removable portion 52B, images acquired by the observation section 56a are processed by the main control section 62 and then displayed on the display unit 13 (see FIG. 9).

Here, as is shown in FIG. 8, a first local coordinate system (a first orthogonal coordinate system) $W_1$, which is an orthogonal coordinate system that faces the distal end side of the treatment portion 203, and whose original point $O_1$ is prescribed on the treatment portion 203 of the surgical instrument 200, is prescribed. Namely, a $Z_1$ axis of this first local coordinate system $W_1$ faces the distal end side of the treatment portion 203 with the treatment portion 203 taken as an original point. In the same way, a second local coordinate system (a second orthogonal coordinate system) $W_2$, which is an orthogonal coordinate system that faces the distal end side along the optical axis C2, and whose original point $O_2$ is prescribed on the observation section 56a of the endoscope 56, is prescribed. Namely, a $Z_2$ axis of this second local coordinate system $W_2$ faces the distal end side along the optical axis C2 with the observation section 56a taken as an original point.

Conversions from the first local coordinate system W1 to the second local coordinate system W2 are expressed using a conversion matrix A, as is commonly known.

The slave control section 63 calculates a converted operating command by using the conversion matrix A to convert an operating command that was issued by the master manipulator 10 and that shows the target position and target orientation on the global coordinate system $W_0$, and then controls the removable portion drive section 28A based on this converted operating command.

According to the surgical support apparatus 2 of the present embodiment that has the above described structure, it is possible to reduce the number of sensors that are required to detect the position and orientation of the forceps portion 203.

Furthermore, by performing coordinate conversion such that the orientation of the distal end side of the optical axis C2 of the endoscope 56 matches the orientation of the distal end side of the treatment portion 203, it becomes easy to match the orientation of the distal end of the treatment portion 203 (the treatment portion 203) that appears in the image displayed on the display unit 13, with the orientation of the master manipulator 10. Accordingly, an operability of the master manipulator 10 while viewing the images displayed on the display unit 13 can be improved.

Note that, in the present embodiment, the surgical support apparatus 2 is provided with the slave manipulator 20B, and the endoscope 56 is able to be removably attached to the removable portion 52B of the slave manipulator 20B. However, the slave manipulator 20B is not essential structure in the surgical support apparatus 2, and it is sufficient for the surgical support apparatus 2 to be provided with the endoscope 56 and the display unit 13. This is because the same effects as those demonstrated by the present embodiment can be obtained irrespective of where the endoscope 56 is attached.

However, if the surgical support apparatus 2 is provided with the slave manipulator 20B, and if the endoscope 56 is removably attached to the slave manipulator 20B, then the operability of the observation section 56a of the endoscope 56 can be improved.

Third Embodiment

Next, a third embodiment of the present invention will be described with reference made to FIG. 10 and FIG. 11. Note that the same symbols are used for portions that are the same as those in the above described embodiments, and any description thereof is omitted. Only points of difference therefrom will be described.

Figure 10:
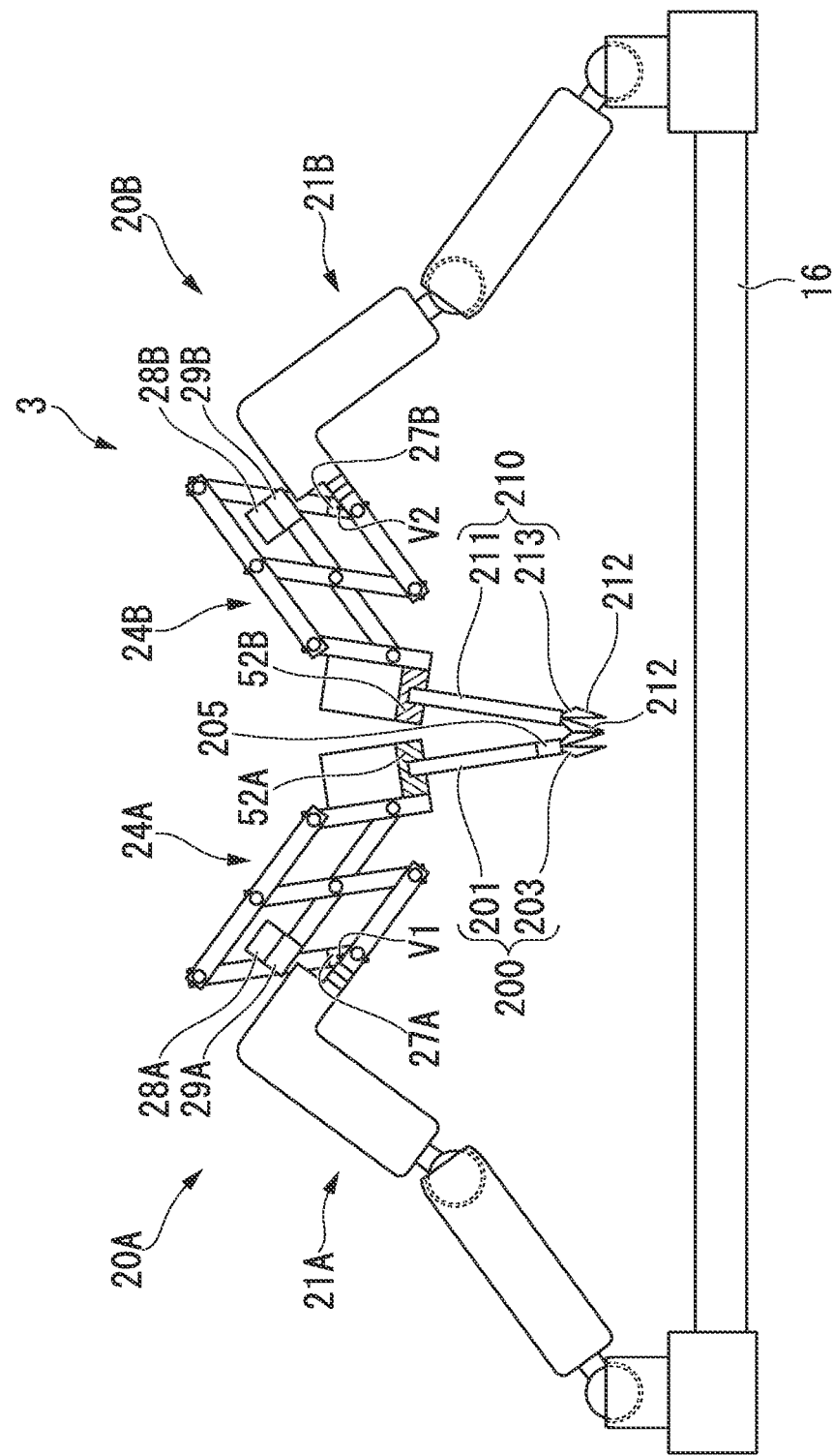
FIG. 10 is a side view of a slave manipulator in a surgical support apparatus of a third embodiment of the present invention.
Figure 11:
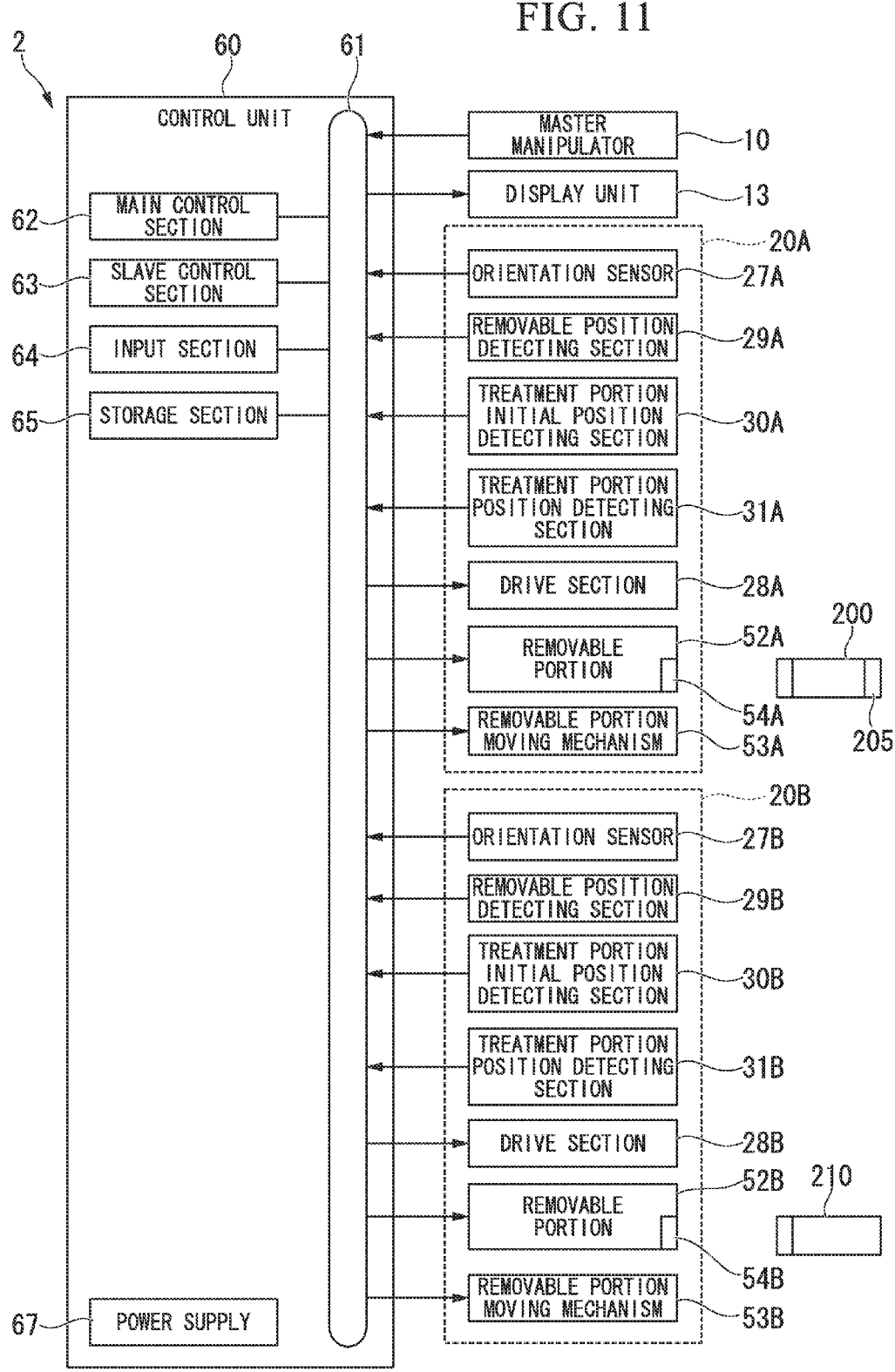
FIG. 11 is a block diagram of the same surgical support apparatus.

As is shown in FIG. 10 and FIG. 11, in a surgical support apparatus 3 of the present embodiment, in addition to the respective component elements of the surgical support apparatus 1 of the first embodiment, there is also provided a slave manipulator 20B (a second medical manipulator) of the present invention that has the removable portion 52B to which a surgical instrument (a second surgical instrument) 210 can be removably attached.

Namely, the surgical support apparatus 3 is provided with two slave manipulators, namely, the slave manipulator (the first medical manipulator) 20A and the slave manipulator 20B.

A contact sensor (a transmitting portion) 205 is provided on a distal end portion of the surgical instrument insertion portion 201 of the above-described surgical instrument (the first surgical instrument) 200.

A storage section 65 is provided in the control unit 60 (see FIG. 11).

The structure of the second surgical instrument 210 is not particularly restricted provided that the structure is rigid, however, in the present embodiment, the same forceps as those in the above-described surgical instrument 200 are used. Namely, in the second surgical instrument 210, a forceps portion (a treatment portion) 213 that is formed by a pair of forcep pieces 212 is provided on the distal end portion of the surgical instrument insertion portion 211.

The contact sensor 205 that is provided on the surgical instrument 200 is a sensor detects that external force is applied to the forceps portion 203. When the forceps portion 203 of the surgical instrument 200 and the forceps portion 213 of the surgical instrument 210 are in contact, the contact sensor 205 transmits a control signal to the slave control section 63 and the storage section 65 via the removable portion-side electrical contact point 54A of the removable portion 52A.

The slave control section 63 calculates a relative positional relationship between the reference position V1 and a reference position V2 from the position and orientation of the forceps portion 203 relative to the reference position V1 when the control signal was received, and from the position and orientation of the forceps portion 213 relative to the reference position V2 when the control signal was received.

The storage section 65 is formed by memory or the like, and the relative positional relationships between the reference position V1 and the reference position V2 that have been calculated by the slave control section 63, namely, the relative positional relationships between the slave manipulator 20A and the slave manipulator 20B are stored therein.

Next, an operation of the surgical support apparatus 3 of the present embodiment that has the above described structure will be described.

The surgical support apparatus 3 is activated, the surgical instrument 200 is attached to the removable portion 52A of the slave manipulator 20A, and the surgical instrument 210 is attached to the removable portion 52B of the slave manipulator 20B. After the slave arms 21A and 21B have been deformed to the desired shape, both of the slave arms 21A and 21B are placed in fixed mode.

The user Q operates the pair of master manipulators 10 and drives the removable portion drive sections 28A and 28B using the slave control section 63 so that the forceps portion 203 of the surgical instrument 200 and the forceps portion 213 of the surgical instrument 210 are brought into contact with each other. As a result of this, the contact sensor 205 detects that an external force has been applied to the forceps portion 203 and transmits a control signal to the storage section 65. The storage section 65 then stores the positions and orientations of the forceps portions 203 and 213 at the point when the forceps portion 203 and the forceps portion 213 came into contact with each other respectively as the contact position and contact orientation of the forceps portion 203 and as the contact position and contact orientation of the forceps portion 213.

Next, the user Q drives the removable portion drive sections 28A and 28B using the slave control section 63. At this time, the slave control section 63 calculates the ranges of movement of the slave manipulator 20A and the slave manipulator 20B based on the calculated relative positional relationship between the reference position V1 and the reference position V2, and controls the forceps portion 203 and the forceps portion 213, or alternatively controls the slave manipulator 20A and the slave manipulator 20B such that they do not interfere with each other.

Specifically, when the user Q issues an operating command that will cause the forceps portions 203 and 213 or the slave manipulators 20A and 20B to come into contact with each other, the slave control section 63, for example, stops the operations of the removable portion drive sections 28A and 28B, and, preferably, also emits a display or sounds that signify a warning urging the user Q to take care.

According to the surgical support apparatus 3 of the present embodiment that has the above described structure, it is possible to reduce the number of sensors that are required to detect the position and orientation of the forceps portion 203.

Furthermore, as a result of the slave control section 63 being provided with the contact sensor 205 and the storage section 65 and performing control in the manner described above, the slave control section 63 is able to recognize the relative positions between the slave manipulators 20A and 20B when the forceps portion 203 and the forceps portion 213 come into contact with each other, and is able to recognize how the ranges of movement of the respective slave manipulators 20A and 20B may interfere with each other, and the like.

In addition, the slave control section 63 is able to perform control so as to prevent the movements of the slave manipulators 20A and 20B from interfering with each other, such as by not allowing them to come into contact with each other or the like.

In the present embodiment, the contact sensor 205 is used as a transmitting portion, however, any desired component may be used provided that it is able to transmit a control signal to the storage section 65 when the forceps portion 203 of the surgical instrument 200 and the forceps portion 213 of the surgical instrument 210 come into contact with each other. The transmitting portion may have a variety of structures such as those described below.

For example, it is also possible to provide as the transmitting portion a source for generating imperceptible vibrations, and to provide an amplitude detecting sensor that detects the amplitude of these vibrations on the distal end portion of the surgical instrument insertion portion 201 of the surgical instrument 200. When the forceps portion 213 comes into contact with the forceps portion 203, which is vibrating at a fixed amplitude, the amplitude of the forceps portion 203 changes. Because of this, it is possible to detect whether or not the forceps portion 213 is in contact with the forceps portion 203.

It is also possible to provide as a transmitting portion an ultrasonic wave generating source that generates ultrasonic waves, and to provide an ultrasonic wave receiving portion that detects the ultrasonic waves reflected by the forceps portion 213.

It is also possible to detect whether or not the forceps portion 213 is in contact with the forceps portion 203 by acquiring images of the area around the forceps portion 203 using an imaging element such as a CCD, and then analyzing these images using commonly known image processing technology.

It is also possible to construct the transmitting portion using switches and the like. In this case, an assistant or the like observes the area around the forceps portion 203 using an endoscope, and when the forceps portion 203 and the forceps portion 213 come into contact with each other, the assistant operates a switch so as to transmit a control signal to the storage section 65.

First through third embodiments of the present invention have been described above in detail with reference made to the drawings, however, the specific structure thereof is not restricted to these embodiments and various structural modifications and the like may be made insofar as they do not depart from the spirit or scope of the present invention. Furthermore, it should be understood that each of the component elements described in each of the embodiments may also be used in various suitable combinations with each other.

Figure 12:
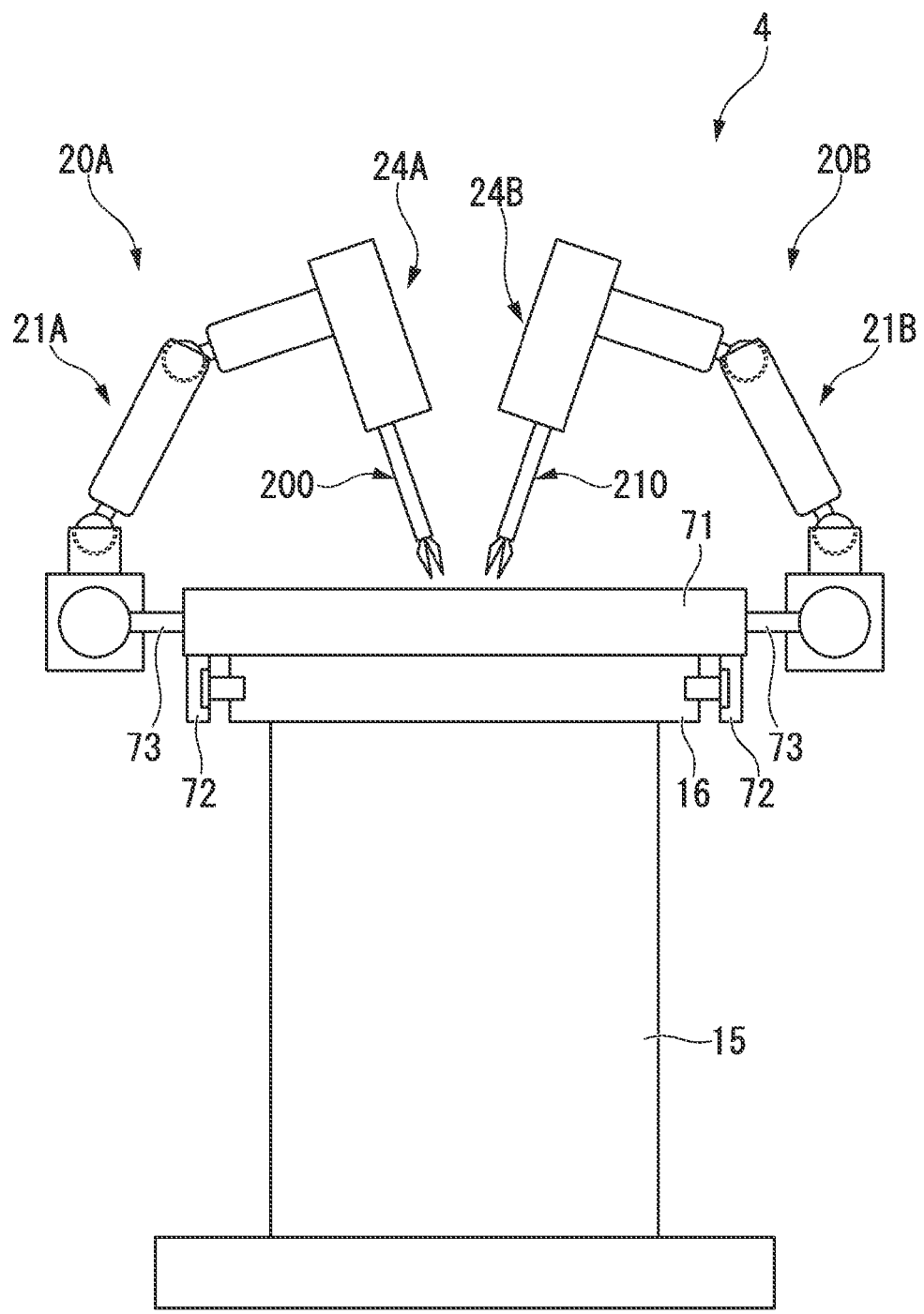
FIG. 12 is a side view of a surgical support apparatus in an embodiment of a modified example of the present invention.

For example, in the above described first through third embodiments, the slave manipulator 20A is fixed to the surgery top board 16, however, it is also possible to employ a structure such as the surgical support apparatus 4 shown in FIG. 12. Namely, in the surgical support apparatus 4, a robot top board 71 is fixed to the surgery top board 16 of an operating table 15 using connecting tools 72, and the slave manipulators 20A and 20B are fixed to a pair of guide rails 73 that are provided at side surfaces of this robot top board 71.

Note that, in FIG. 12 and subsequent drawings, the above-described parallel link is drawn in the shape of a box in order to simplify the description.

Each guide rail 73 extends orthogonally to the surface of the paper showing the drawing of FIG. 12, and the slave manipulators 20A and 20B are able to be slid to a desired position in the longitudinal direction of the guide rails 73 and then fixed in that state. Namely, information about the relative positions of the slave manipulators 20A and 20B can be set in the storage section or the like of the control unit 60 as constraint conditions for the slave manipulators 20A and 20B.

Note that, in the present modified example, the two slave manipulators 20A and 20B are provided on the surgical support apparatus 4, however, the number of slave manipulators provided on the surgical support apparatus 4 is not restricted and it is also possible for one slave manipulator, or three or more slave manipulators to be provided. This also applies to the first through third embodiments.

Figure 13:
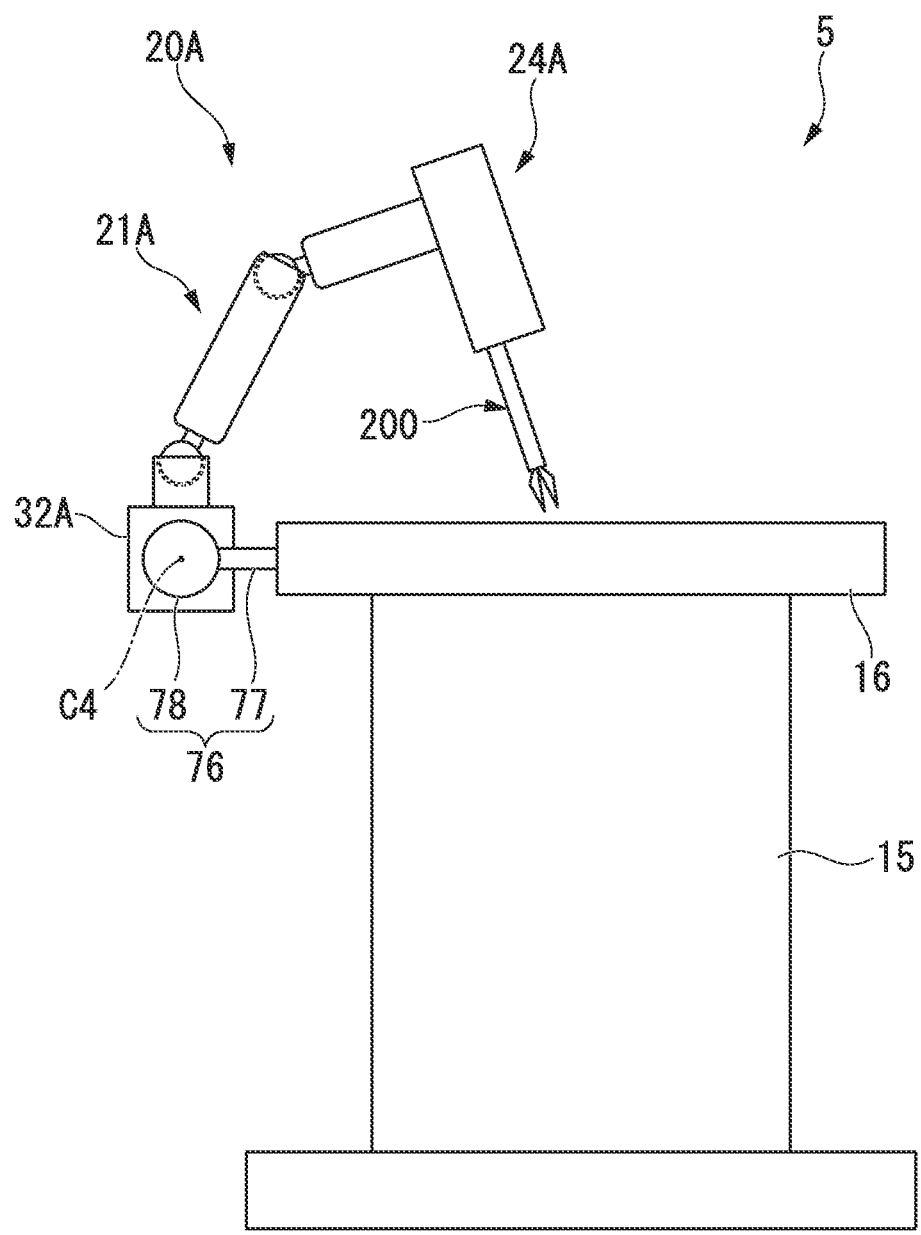
FIG. 13 is a side view of a surgical support apparatus in an embodiment of a modified example of the present invention.
Figure 14:
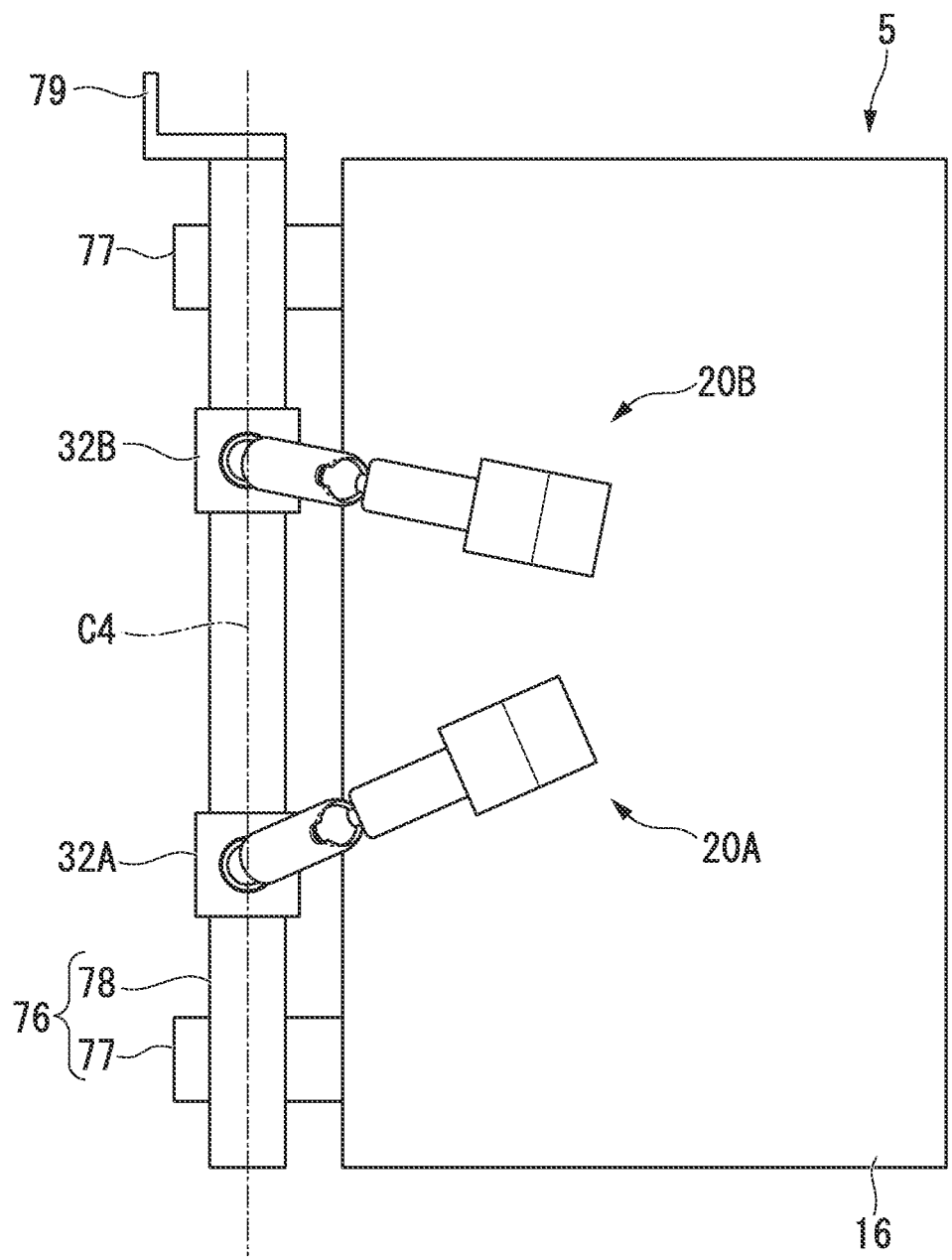
FIG. 14 is a plan view of the same surgical support apparatus.

As in a surgical support apparatus 5, which is shown in FIG. 13 and FIG. 14, it is also possible for the slave manipulators 20A and 20B to be fixed via a rotating mechanism 76 that is provided at a side surface of the surgery top board 16.

The rotating mechanism 76 has a known structure, and has a pair of supporting components 77 that are provided at a side surface of the surgery top board 16, and a head rail 78 that is supported by the supporting components 77 such that being turnable around its own axis C4. The head rail 78 can be switched by means of a fixing mechanism (not shown) that is provided on the supporting components 77 between a turning mode in which it is able to turn around the axis C4 relative to the supporting components 77, and a restricted mode in which this turning is restricted.

A handle 79 is attached to one end portion of the head rail 78.

The stand 32A of the slave manipulator 20A and the stand 32B of the slave manipulator 20B are fixed to the head rail 78.

Using the surgical support apparatus 5 of the present modified example that has the above described structure, the surgical instrument 200 is attached to the slave manipulator 20A, and treatment is performed by introducing the surgical instrument 200 into the interior of the body cavity P3 of the patient P. At this time, the slave arm 21A is placed in fixed mode, and the fixing mechanism is placed in restricted mode.

While treatment is being performed, in some cases, it is necessary for the surgical instrument 200 to be immediately extracted from the patient P.

Figure 15:
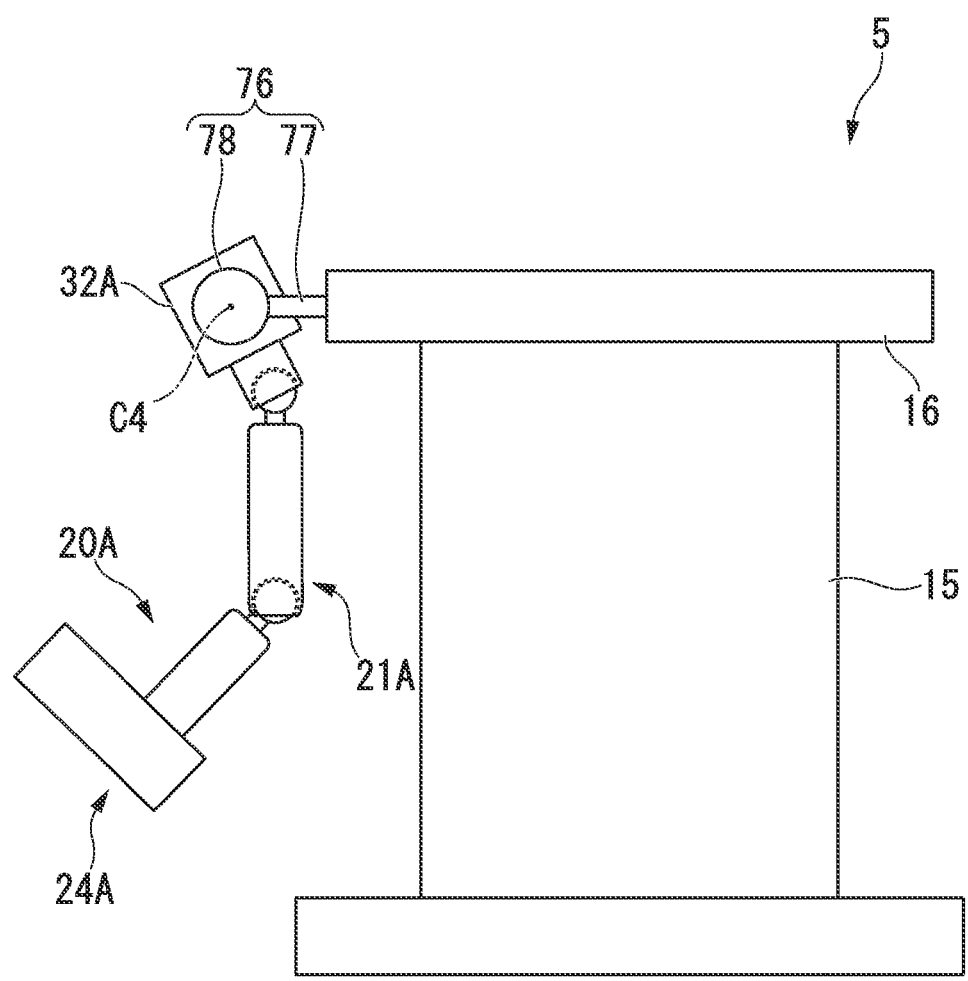
FIG. 15 is a side view showing when the slave manipulator of the same surgical support apparatus has been retreated.

In cases such as this, after an assistant has extracted the surgical instrument 200 from the interior of the body cavity P3, the assistant removes the surgical instrument 200 from the slave manipulator 20A, and switches the fixing mechanism to turning mode. The assistant then grips the handle 79 and, as is shown in FIG. 15, turns the head rail 78 around the axis C4, so that the slave manipulator 20A and the slave manipulator 20B are withdrawn from above the surgery top board 16 to a position below the surgery top board 16.

According to the surgical support apparatus 5 of the present modified example that has the above described structure, it is possible to rapidly withdraw the slave manipulators 20A and 20B from above the surgery top board 16.

In the above described first embodiment through third embodiment, the positioning arm is provided with a parallel link. However, in cases such as abdominal surgery and the like in which it is not necessary for the surgical instrument to pass through a steady point, the positioning arm may not be provided with a parallel link.

Moreover, in cases such as when it is possible to easily deduct the position and orientation of the forceps portion of the surgical instrument that is attached to the removable portion from the position and orientation of the removable portion, and then perform an operation using the master manipulator 10, it may not necessary for the treatment portion position detecting section to be provided.

The removable portion 52A has been set on the second side element 47A, however, the removable portion 52A may also be set on the second side elements 45A or 46A.

The slave arms are made by connecting shaft bodies together by means of ball joints, however, the slave arms are not restricted to this structure. Provided that the slave arms have three or more degrees of freedom, then it is also possible, for example, for the slave arms to be made from a plurality of linear guides and articulated joints.

In addition to this, the present invention is not limited by the foregoing description, and is only limited by the scope of the appended claims.

What is claimed is:

1. A surgical support apparatus comprising:
   a surgical instrument having a treatment portion;
   a holding portion whose proximal end portion is connected to a base;
   a positioning portion that has a pair of first side elements rotatably connected to a proximal second side element and rotatably connected to a distal second side element;
   a parallel link mechanism in which the pair of first side elements are disposed parallel each other, the distal second side element and the proximal second side element being disposed substantially parallel to each other and non-parallel with respect to the pair of first side elements;
   the proximal second side element which is rotatable with respect to a distal end portion of the holding portion, and the distal second side element which has a removable portion to which the surgical instrument is able to be attached;
   an input section that generates operating commands based on inputs from a user;
   a reference orientation detecting portion that detects an orientation of a reference position on the positioning portion according to the operating commands:
   a removable position detecting section provided at the proximal second side element, the removable position detecting section calculating an amount of change in position and orientation per unit time of the removable portion by calculating a position and orientation of the removable portion with respect to the reference position according to a detected orientation of the reference position detected by the removable position detecting section;
   a treatment portion position detecting section which calculates a position and orientation of the treatment portion based on a length of the surgical instrument in a longitudinal direction of the surgical instrument and the amount of change calculated by the removable position detecting section; and
   a drive section control section which controls a drive section actuating the removable portion and the treatment portion based on calculating results of the removable position detecting section and the treatment portion position detecting section.

2. The surgical support apparatus according to claim 1, wherein
   the holding portion is able to be switched between
   an adjustment mode in which a position of the distal end portion relative to the proximal end portion is able to be adjusted, and
   a fixed mode in which the position of the distal end portion relative to the proximal end portion is fixed.

3. The surgical support apparatus according to claim 1, wherein the reference orientation detecting portion transmits the detected orientation of the reference position by wireless communication to the section treatment portion position detecting section.

4. The surgical support apparatus according to claim 1, further comprising:
   an endoscope that is provided with an observation portion that is used to acquire external images along an optical axis; and
   a display unit that is used to display the images, wherein
   the drive section control section calculates converted operating commands by converting the operating commands issued by the input section using a conversion matrix that converts these operating commands from a first orthogonal coordinate system that faces a distal end side of the treatment portion into a second orthogonal system that faces the distal end side along the optical axis of the observation portion, and then controls the drive section based on the converted operating commands.

5. The surgical support apparatus according to claim 1, further comprising:
   a plurality of holding portions; and
   positioning portions that are fixed to each one of the holding portions, wherein
   one of the reference orientation detecting sections is able to be removably attached to each one of the positioning portions.

6. A surgical support apparatus comprising:
   a surgical instrument having a treatment portion;
   a holding portion whose proximal end portion is connected to a base;
   a positioning portion that has a pair of first side links rotatably connected to a proximal second side link and rotatably connected to a distal second side link;
   a parallel link mechanism in which the pair of first side elements are disposed parallel each other, the distal second side element and the proximal second side element being disposed substantially parallel to each other and non-parallel with respect to the pair of first side elements;
   the proximal second side link which is rotatable with respect to a distal end portion of the holding portion, and the distal second side link which has a removable portion to which the surgical instrument is able to be attached;
   a controller that generates operating commands based on inputs from a user;
   a reference orientation detecting sensor that detects an orientation of a reference position on the positioning portion according to the operating commands; and
   a removable position detecting sensor provided at the proximal second side link wherein the controller is further configured to implement:
> calculating an amount of change in position and orientation per unit time of the removable portion by calculating a position and orientation of the removable portion with respect to the reference position according to a detected orientation of the reference position detected by the removable position detecting sensor;
>
> calculating a position and orientation of the treatment portion based on a length of the surgical instrument in a longitudinal direction of the surgical instrument and the amount of change calculated by the removable position detecting sensor; and
>
> controlling a drive section actuating the removable portion and the treatment portion based on results of the calculated amount of change in position and orientation per unit time of the removable portion and position and orientation of the treatment portion.

* * * * *